United States Patent
Jakober et al.

(10) Patent No.: US 10,710,851 B2
(45) Date of Patent: Jul. 14, 2020

(54) TELESCOPIC COLUMN

(71) Applicant: Aktiebolaget SKF, Gothenburg (SE)

(72) Inventors: Dieter Jakober, Münchenstein (CH); Daniel Greilinger, Rothenfluh (CH); Marcel Soltermann, Sankt Pantaleon (CH)

(73) Assignee: Aktiebolaget SKF, Gothenburg (SE)

( * ) Notice: Subject to any disclaimer, the term of this patent is extended or adjusted under 35 U.S.C. 154(b) by 269 days.

(21) Appl. No.: 15/935,705

(22) Filed: Mar. 26, 2018

(65) Prior Publication Data
US 2018/0312378 A1    Nov. 1, 2018

(30) Foreign Application Priority Data

Apr. 28, 2017    (DE) .......................... 10 2017 207 249

(51) Int. Cl.
*B66D 5/16*    (2006.01)
*F16B 7/14*    (2006.01)
*A61B 6/00*    (2006.01)

(52) U.S. Cl.
CPC .................. *B66D 5/16* (2013.01); *F16B 7/14* (2013.01); *A61B 6/4464* (2013.01)

(58) Field of Classification Search
CPC ........ A61B 6/4464; B66D 5/16; F16B 7/1481
See application file for complete search history.

(56) References Cited

U.S. PATENT DOCUMENTS

| | | | | |
|---|---|---|---|---|
| 2,123,364 A | * | 7/1938 | Katterjohn .............. | E21B 44/08 173/113 |
| 2,622,450 A | * | 12/1952 | Gorske ..................... | F16H 3/08 74/368 |
| 2,885,896 A | * | 5/1959 | Hungerford, Jr. ........ | F16H 9/04 474/70 |
| 2,967,499 A | * | 1/1961 | Cohen .................... | D05B 69/22 112/275 |
| 3,011,605 A | * | 12/1961 | Hungerford, Jr. ........ | F16B 1/04 192/223.4 |
| 3,175,085 A | * | 3/1965 | Avery .................. | A61B 6/4464 378/197 |
| 3,272,452 A | * | 9/1966 | Cohen .................. | G11B 15/662 242/574 |
| 3,281,598 A | * | 10/1966 | Hollstein ............... | A61B 6/587 378/179 |
| 3,902,070 A | * | 8/1975 | Amor, Jr. ............... | A61B 6/102 378/194 |

(Continued)

Primary Examiner — Emmanuel M Marcelo
(74) Attorney, Agent, or Firm — Laurence A. Greenberg; Werner H. Stemer; Ralph E. Locher

(57) ABSTRACT

A telescopic column includes at least two linearly movable telescopic elements and a drive system. The drive system includes a drive unit having a first clutch element and an output unit having a shaft, a windable connecting element and a second clutch element connected to the shaft such that the clutch element and the shaft rotate together. The drive system includes a brake unit configured to transmit a retaining force onto the second clutch element and configured such that applying a drive moment to the first clutch element reduces the retaining force and allow the telescopic elements to move relative to each other. The brake unit is further configured such that applying an output-side torque to the second clutch element increases the retaining force acting on the second clutch element.

13 Claims, 20 Drawing Sheets

(56) References Cited

U.S. PATENT DOCUMENTS

| | | | | | |
|---|---|---|---|---|---|
| 4,278,003 | A | * | 7/1981 | Hanson | G10D 13/023 84/411 A |
| 4,428,710 | A | * | 1/1984 | Grisebach | B25J 9/04 414/590 |
| 4,728,072 | A | * | 3/1988 | Mitchell | A47C 3/28 248/406.1 |
| 4,860,987 | A | * | 8/1989 | Werner | A47C 3/24 248/405 |
| 4,901,339 | A | * | 2/1990 | Heinz | F16M 11/18 248/332 |
| 5,303,443 | A | * | 4/1994 | Alexander | B65G 69/2841 14/71.1 |
| 7,810,793 | B1 | * | 10/2010 | Chiang | B66F 3/10 211/117 |
| 2006/0130713 | A1 | * | 6/2006 | Jones | A47B 9/00 108/106 |
| 2018/0312377 | A1 | * | 11/2018 | Jakober | B66D 5/00 |
| 2018/0314053 | A1 | * | 11/2018 | Jakober | G02B 15/14 |

\* cited by examiner

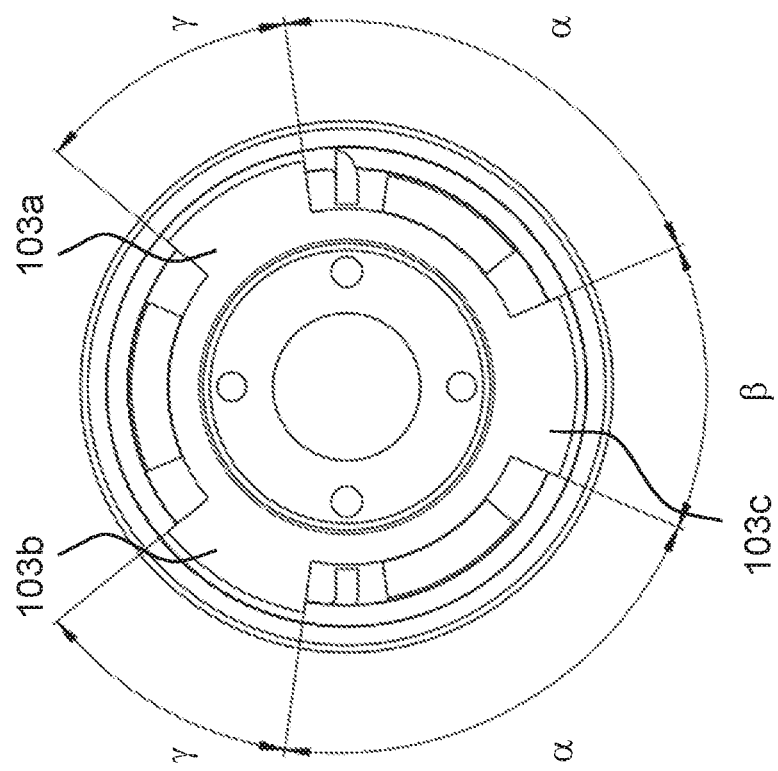
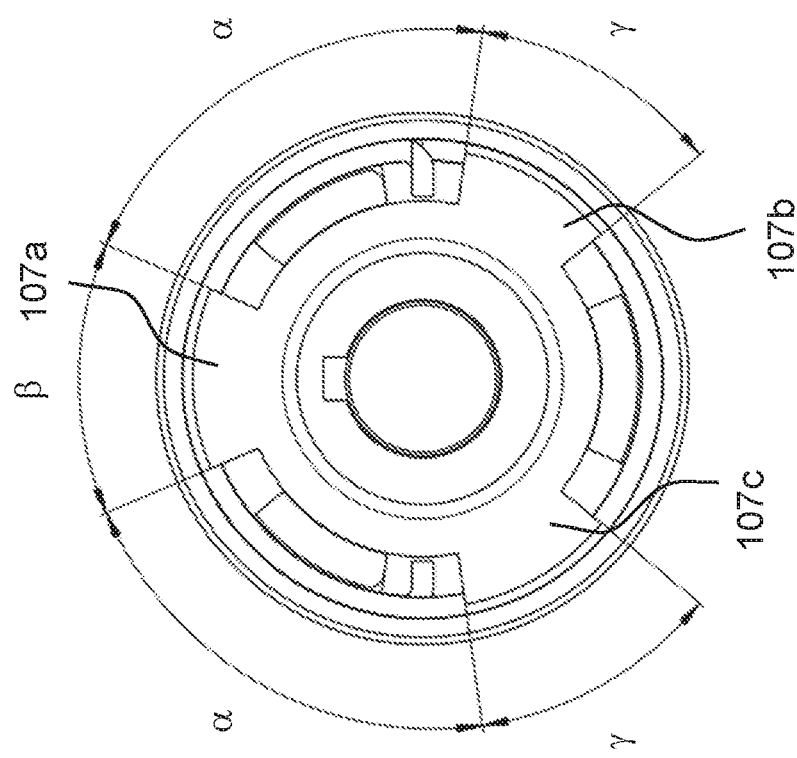
Fig. 12

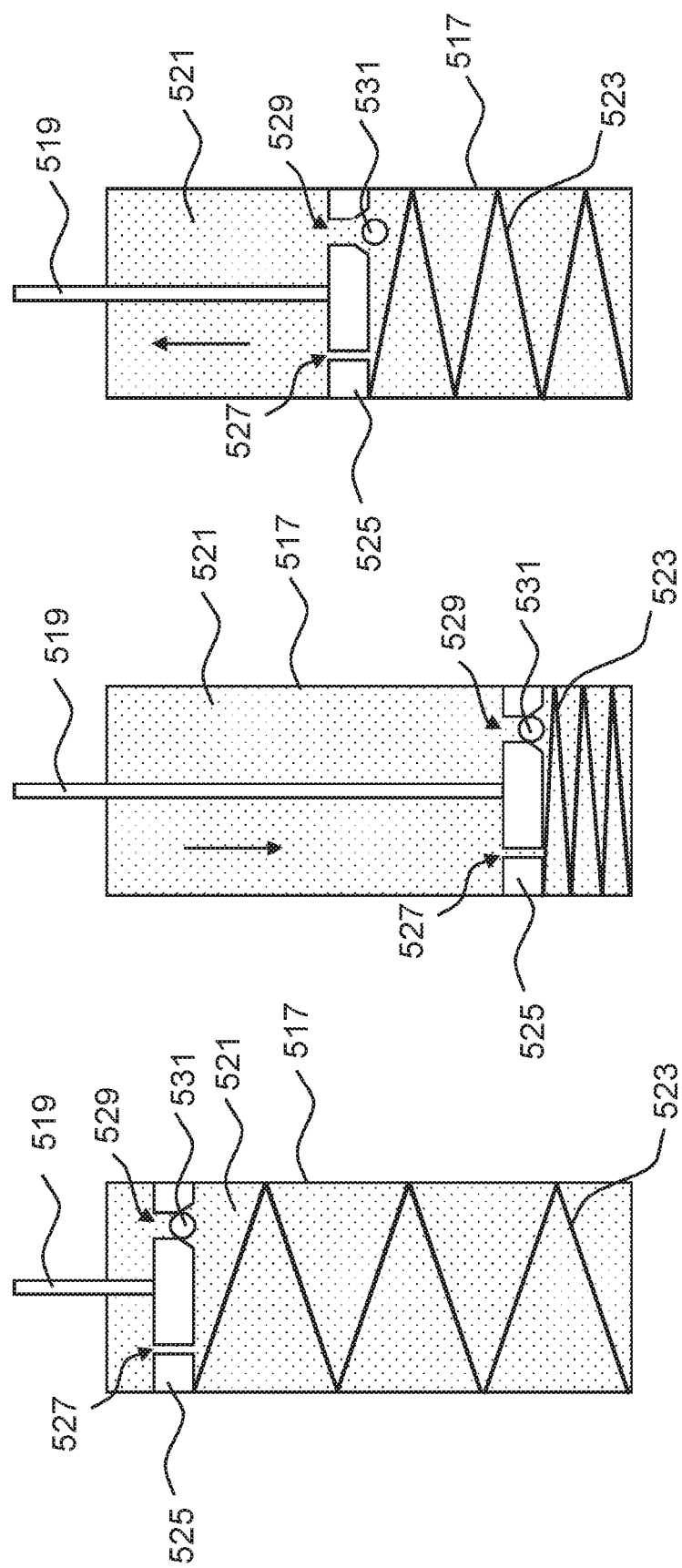

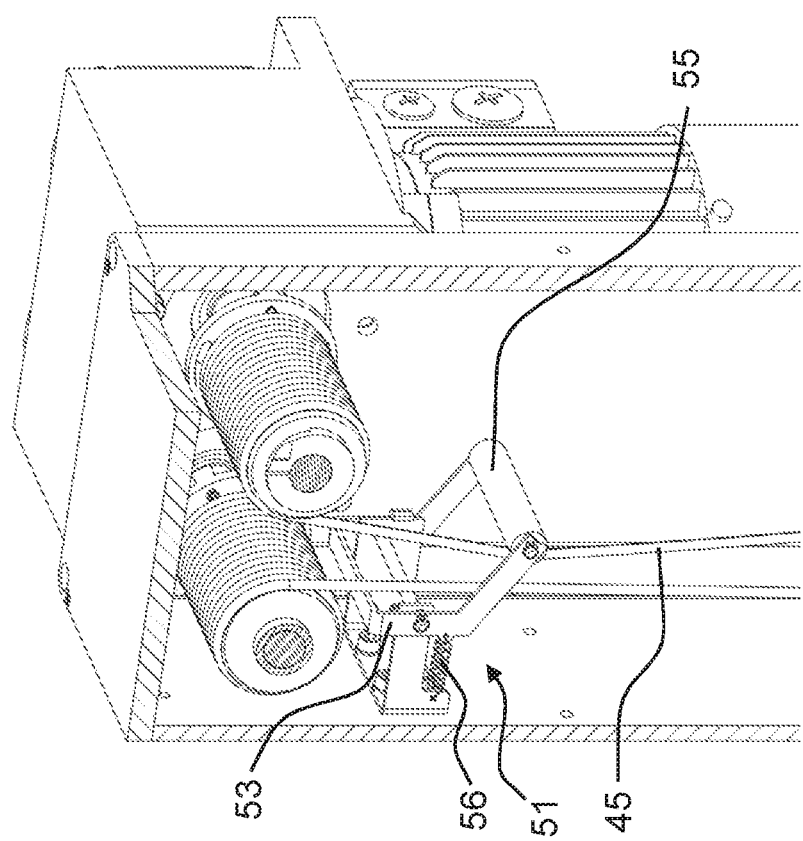
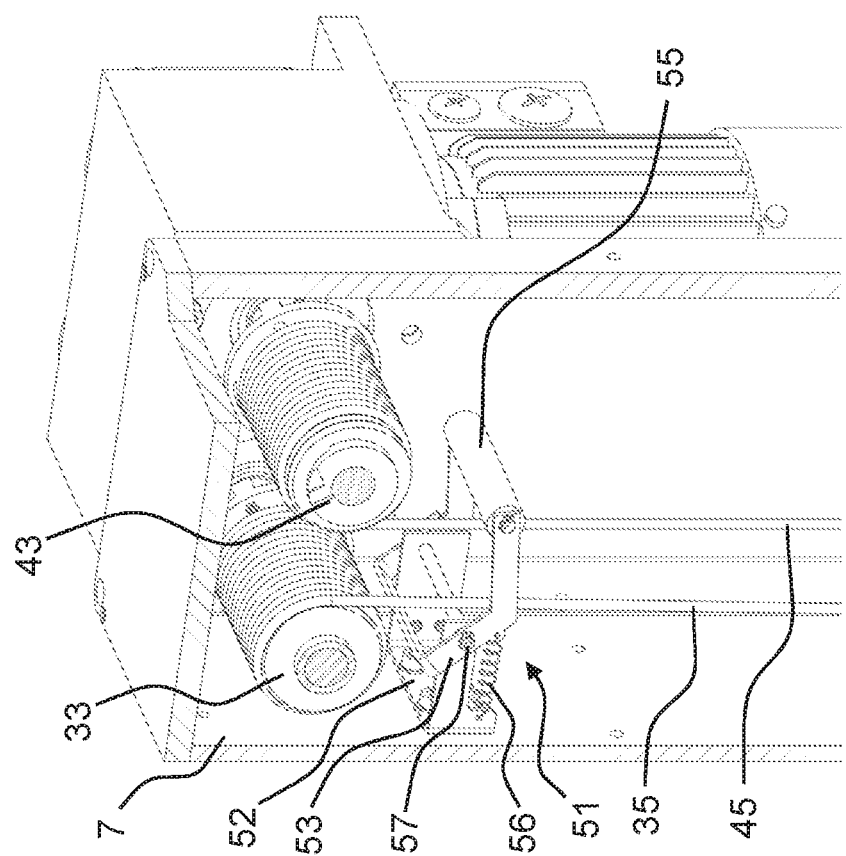

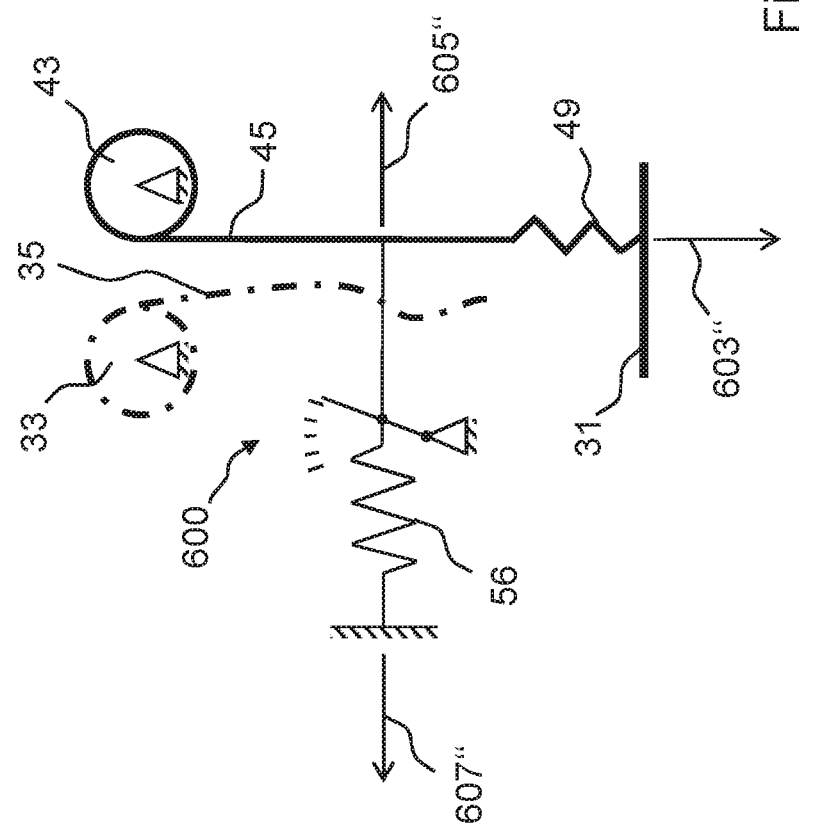

TELESCOPIC COLUMN

CROSS-REFERENCE

This application claims priority to German patent application no. 10 2017 207 249.0 filed on Apr. 28, 2017, the contents of which are fully incorporated herein by reference.

TECHNOLOGICAL FIELD

The disclosure relates to a telescopic column.

BACKGROUND

Telescopic columns are used in numerous areas of technology. Using a telescopic column, an object or a device can be brought into different positions. In typical embodiments the telescopic column includes a plurality of round, or right-angled, or polygonal column elements lying one-inside-another, often configured tubular, which are retractable and extendable with respect to one another by a motor-driven mechanism. Respective directly adjacent tubes have a maximum extendability so that to maintain the stability a certain overlap of the tubes is always ensured. A distinction is made here between telescopic columns that are positioned on the ground and those that are attached to a ceiling. While the former are used, for example, in operating tables and make possible an upward and downward movement of the table, the latter are attached to the ceiling or a stand, for example, for movably securing X-ray machines. The X-ray machine is thus movable in height. In addition, another multiple-member arm can be attached between the telescopic columns, which multiple-member arm additionally makes possible a horizontal movement.

SUMMARY

In particular, ceiling-hanging telescopic columns are often equipped with complex cable drives that occupy correspondingly large installation volumes. At the same time there are strict safety requirements especially in the medical field. It is an aspect of the disclosure to provide a telescopic column that is compact and simple and that simultaneously satisfies strict safety standards.

This is achieved by a telescopic column according to embodiments of the disclosure.

One embodiment of the disclosure relates to a telescopic column, including at least two telescopic elements linearly movable with respect to each other, further comprising a drive system comprising the following features:
  a drive unit including a first clutch element,
  a drive unit including a shaft, a windable connecting element, and a second clutch element connected to the shaft such that the clutch element and the shaft rotate together, wherein the connecting element is connected to the shaft and at least one of the movable telescopic elements,
  a brake unit that is configured such that a sufficiently strong holding force is transmissible onto the second clutch element that the telescopic elements are held in their relative position with respect to each other,
  the brake unit is further configured such that applying a drive torque against the first clutch element reduces the holding force such that the telescopic elements are movable relative to each other, and
  the brake unit is further configured such that applying an output-side drive torque against the second clutch element increases the holding force acting on the second clutch element.

The brake unit offers a high degree of safety, such as is required in particular in medical applications, with compact design. The two clutch elements are preferably manufactured from steel or a comparably durable material and can be made compact. A distinction is made in the disclosure between the drive side and the output side. In order to move the telescopic elements, i.e., for retracting or extending the telescopic column, a force generated by the drive unit, for example, by a motor, is transmitted to the first clutch element. This is, for example, set into rotation. The flow of force taking place up to now defines the drive side and a drive-side force or a drive-side torque. Due to the always-acting gravitational force, in the event of a lack of a corresponding counter-force there is the tendency in a telescopic column in most operating states for the relative positions of the telescopic elements to change with respect to one another. This is always the case in ceiling-hanging telescopic columns when the telescopic column is not fully extended. In the fully extended state, retaining elements usually stabilize the telescopic elements with respect to one another so that the telescopic column does not fall apart. As long as the telescopic column is not fully extended, the gravitational force must be compensated elsewhere. Gravity produces a force on the telescopic elements, which exert a force on the shaft through the connecting element and thus on the second clutch element connected thereto. This flow of force defines the output side of the telescopic column. If the output-side torque were not compensated, the telescopic column would move in an uncontrolled manner into its fully extended state. However, due to the permanently present retaining force, in the event of the absence of a drive-side torque the brake unit compensates the output-side torque, so that the telescopic column can be held in any position. For this purpose no drive-side force is required, so that the drive unit only need be activated for operation. The torque permanently acting on the drive-side in the not-fully-extended state additionally increases the retaining force, so that even with an increase of the load no uncontrolled extending occurs. In contrast to known systems, the drive system has extremely compact dimensions and a mechanically simple realizability. In addition, it meets the high safety standards in the medical field. However, embodiments of the disclosure are also usable in other areas, for example, in production facilities or workshops.

If the telescopic column is to be retracted, then a drive-side torque is generated, whereby the retaining force is reduced. Simultaneously the two clutch elements can preferably come into operative contact so that the torque is transmitted onto the shaft and the connecting element is wound up. The direction of the torque is to be chosen accordingly. The telescopic column is subsequently retracted. Conversely if the telescopic column is to be extended, then a drive-side torque is generated in the other direction, whereby the retaining force is also reduced. Simultaneously the connecting element is unwound and with assistance of the gravitational force the telescopic column is extended.

For telescopic columns located on the ground, often referred to as lifting columns, the embodiments apply correspondingly reversed with respect to the interaction of the drive with the gravitational force, so that here with extending of the telescopic column the gravitational force is worked against, and with retracting the gravitational force is worked with. Otherwise all advantages and constructive features mentioned in the embodiments of the disclosure described here can also be transferred to lifting columns and used analogously with slight modifications.

In preferred embodiments of the disclosure one of the telescopic elements is fixedly connected to or positioned with the ceiling or the floor of a space. It can be, for example, a treatment space or a workshop space. It is also possible that the telescopic element is connected to a frame. The second or the plurality of further telescopic elements are respectively linearly movable with respect to the first telescopic element and extendable therefrom or retractable thereinto. The telescopic elements lie nested one-inside-the-other with decreasing outer-diameter or -circumference. The drive unit is preferably connected to the supported or fixed telescopic element. The connecting element transmits a force generated by the drive unit to the second or the innermost of the telescopic elements and thus makes possible a retracting and extending of the telescopic column. The innermost of the telescopic elements here causes a retracting or an extending of the remaining telescopic elements, if present. Alternatively the force transmission can also be effected directly on all further telescopic elements, so that they are movable directly by the drive unit. This would be advantageous, for example, in synchronized telescopic columns.

In one preferred embodiment of the disclosure the connecting element is embodied as a cable, belt, or chain. This makes possible a simple and cost-effective and, here, reliable and secure force transmission. The connecting element is preferably connected to the shaft such that with rotation of the shaft it is windable or unwindable. Embodiments including steel cables are particularly preferred.

In one preferred embodiment of the disclosure the brake unit includes a spring element and a brake surface, wherein the spring element is configured such that due to a preload it is bringable into frictional contact with the brake surface for generating the retaining force and such that it is bringable into operative contact with the clutch elements and thereby its spring tension is changeable. For example, the clutch elements, the spring element, and the brake unit form a coil spring coupling unit. These make possible a particularly compact design so that little space is to be provided for the drive unit and the brake unit. Simultaneously this embodiment of the disclosure can be adapted to various situations via the dimensioning and design of the spring element and of the housing.

The brake surfaces can be formed, for example, on the inner side of a housing surrounding the spring element. The preload for generating the retaining force presses the round spring element outward against the brake surface. Alternatively, the brake surfaces can be formed on the outer side of an element, for example, of a cylindrical mandrel, that is surrounded by the spring element. Here the preload acts conversely. The following embodiments and advantages are each based on a housing with a spring element lying therein. However, they are transferrable in a simple manner to an outer-lying spring element and a brake element lying therein.

In one preferred embodiment of the disclosure the operative contact between the clutch elements and the spring element is generatable by at least one coupling element formed on each of the clutch elements and at least one coupling element, corresponding thereto, of the spring element. These can be, for example, claw-type extensions, extending axially and lying inside the spring element, which correspond to an extension of the spring element. Rotating the clutch element and the coupling elements causes the latter to press on the extension of the spring element, and in the case of an embodiment as a coil- or wrap-spring, pushes it open or closed depending on the direction of rotation. The spring tension is thus increased or decreased in relation to the surrounding housing. Thus the retaining force of the brake unit can be influenced by the drive unit.

In one preferred embodiment of the disclosure each of the clutch elements includes at least two coupling elements and the spring element includes two coupling elements, each corresponding to one of the coupling elements of the clutch elements, wherein with rotation of the clutch element in the clockwise direction one of the coupling elements of the clutch element respectively enters into operative contact with one of the coupling elements of the spring element, and with rotation of the clutch element in the counterclockwise direction the respective other one of the coupling elements of the clutch elements enters into operative contact with the other coupling element of the spring element, so that independent of the respective direction of rotation of the respective coupling element a changing operative contact analogous to the spring tension is generatable. In this context "analogous" means that the operative contact changes equally or nearly equally, i.e., the retaining force increases or decreases. Thus a drive system for a telescopic column can be provided wherein the force transmission from the drive unit to the brake unit or from the output unit to the brake unit is effected independently of the respective direction of rotation. Consequently the direction of rotation need not be taken into consideration in the construction of a corresponding telescopic column.

This is in particular advantageous in preferred embodiments of the disclosure that comprise a further drive system that is constructed analogously to the first drive system and functions as a redundant drive system. The second drive system can be embodied completely separately. Alternatively and preferably both drive units can be driven via a common motor so that they work synchronously. In this case it can be constructively advantageous to operate both shafts in respectively opposing directions of rotation in order to achieve a compact- and simple-as-possible design. Thus both drive units can be supported, for example, parallel and closely spaced, and be rotated in opposite directions simultaneously via a drive wheel of a motor, which drive wheel lies between them. Alternatively other common drives, such as a bevel gear, spur gear, belt, etc. can be used. Due to the rotational-direction-independent transmission of the operative contact it is ensured that with the transmitting of forces from the respective drive unit to the output unit the same effect, i.e., retracting or extending of the telescopic column, is achieved. Thus one of the drive units can be configured, for example, as a main drive unit, and extend and retract the telescopic column in normal operation. The second drive unit is then embodied as a redundant safety system and performs the movements in parallel. In the case of a failure of the first drive system, for example, by breakage of the connecting element, the gravitational force is directly absorbed by the safety system and an uncontrolled retracting or extending is avoided.

In one preferred embodiment of the disclosure, each of the clutch elements respectively includes at least one third coupling element, wherein the coupling elements of the clutch elements are configured such that one of the coupling elements of both clutch elements is bringable into direct contact as soon as one of the first or second coupling elements of the clutch elements is in operative contact with one of the coupling elements of the spring element. A simultaneous reduction of the retaining force and a direct bringing-into-engagement of the coupling elements is thereby achieved, so that with the reducing of the retaining force the drive- and output-side of the drive are in direct operative contact via coupling elements and a torque of the motor is directly transmitted. The movable telescopic element is then directly held and moved by the motor.

In one alternative embodiment the coupling elements of the clutch elements each have an opening that is configured and disposed such that in the case of operative contact the coupling elements of the spring element are receivable therein such that one of the couple elements of each of the two clutch elements is bringable into operative contact. Analogously in this embodiment a simultaneous reduction of the retaining force and a direct bringing-into-engagement of the coupling elements is achieved, so that with reducing of the retaining force the drive- and output-side of the drive are in direct operative contact and a torque of the motor is directly transmitted.

In some embodiments a stopper is provided mounted end-side in the tubes of telescopic columns, so that the maximum travel is mechanically limited and a respective end position of the movement is fixed. With moving of the tubes with respect to each other, contact with the stopper thus occurs at full speed, which on the one hand stresses the material and on the other hand causes a loud noise. The noise is disruptive in particular in medical applications. In addition, the impact generates a shock that compromises operator comfort, since it acts, for example, on a hand of an operator.

It is therefore a further aspect of the present disclosure to provide a telescopic column that avoids such disadvantages.

This is achieved by a telescopic column according to embodiments of the disclosure.

One embodiment of the disclosure relates to a telescopic column having the following features:
  at least two telescopic elements movable with respect to one another between two end positions,
  at least one damper unit that is configured such that, prior to reaching at least one of the end positions, a force slowing the relative movement of the telescopic elements is exertable on at least one of the telescopic elements.

In embodiments of the disclosure the telescopic elements are linearly movable with respect to one another. In addition, a rotary movement can simultaneously or alternatively be performed. The damper unit is preferably independent from a drive of the telescopic column. The constructive expense is thereby reduced. Due to the damper unit a braking process is reliably introduced by the slowing force prior to the reaching of the end position; the braking force reduces the relative speed of the telescopic elements with respect to one another. Thus any contact with the stopper in the respective end position is with significantly reduced speed. The material is thus spared and loud impact noises avoided. Operating comfort is increased. Alternatively the damper unit can be designed such that a separate stopper is no longer required. In this case the damper unit brakes the movement until stoppage. However, a separate stopper can also additionally be provided in this embodiment. In preferred embodiments the damper unit includes an absorption element, using which the kinetic energy is absorbable. Thus as known with shock absorbers per se, the movement can be efficiently damped and a hard impact as well as vibrations can be avoided.

Preferably the damper unit cooperates with both telescopic elements in order to generate the force. Thus mechanical or electromechanical components of the damper unit can be connected to both telescopic elements and correspondingly designed to cooperate. If further telescopic elements are provided, then in preferred embodiments one or more damper units can respectively be disposed between two of the telescopic elements.

In one preferred embodiment of the disclosure the damper unit is configured such that due to the generated force the movement of the two telescopic elements is continuously slowed until reaching the end position. In this case stoppers are not mandatory. Alternatively stoppers can nevertheless be provided that are redundant, for example, to avoid an uncontrolled extending or retracting of the telescopic column or a separating of the telescopic elements, which could lead to an accident, in the case of a failure of the damper unit. They can additionally relieve the damper unit in the event of extended persistence in the extended state.

In one preferred embodiment of the disclosure the damper unit comprises at least one damping element and a stop, wherein for generating the force the damping element is bringable into operating contact with the stop. This embodiment is mechanically simple and reliable. In addition, a particularly space-saving embodiment can thus be implemented.

The damping element is preferably secured on one of the telescopic elements. This can be effected, for example, using screws or adhesive, which is particularly easily executable. The stop is preferably secured on the other of the telescopic elements such that prior to reaching the end position the stop is bringable into operative contact with the damping element. Thus a reliable and cost-effective damping can be achieved in a constructively simple and space-saving manner.

In one preferred embodiment of the disclosure a further stop is secured on other of the telescopic elements such that prior to reaching the other end position the further stop is bringable into operative contact with the damping element. A damping near both end positions can thus be achieved in a simple manner.

The damping element is preferably retained in a hole-type opening of one of the telescopic elements. This is a particularly space-saving embodiment. It can thus be easy to assemble and disassemble. The stop is then preferably secured on the other of the telescopic elements such that prior to reaching the end position the stop is bringable into operative contact with the damping element. The movement can thus be reliably slowed.

In one preferred embodiment of the disclosure the damping element comprises the following features:
  A housing, wherein a piston is movably disposed,
  A spring element by which a force is generatable between the piston and the housing.

Comparable damping elements are known from other applications, for example in the damping of drawers when closing. They can be produced cost-effectively and compact and according to experience work reliably.

Preferably a cavity filled with a fluid is formed in the housing, in which cavity the spring element and the piston are disposed. The fluid is pressed through a hole-type tapering, integrated in the piston or present separately, into a further cavity. The kinetic energy can thereby be absorbed and the movement damped. This makes possible a particularly uniform slowing and damping of the movement. Preferably here the plunger is bringable into operative contact with the stop. As soon as the telescopic elements are again moved away from one another, the spring element presses the piston back into its initial position again so that in the next process a braking process can take place again.

Alternatively a gas compressible by the plunger can be introduced in the housing so that the kinetic energy can be converted.

In one preferred embodiment of the disclosure the telescopic elements have circumferential measurements adapted to one another and are disposed nested one-inside-the-other such that from the outer- to the inner-lying telescopic element an inner surface of the outer-lying telescopic element respectively corresponds to an outer surface of the next-inner-lying telescopic element via a damper unit, wherein a damping element of the damper unit is respectively secured on the outer surface and a stop of the damper unit is secured on the corresponding inner surface. This is advantageous in particular in telescopic columns having multiple nested telescopic elements, since the braking force on a plurality of the telescopic elements can thus be transmitted by a plurality of damper units. This assembly can also be embodied in reverse.

With the use of a steel cable, a belt, or a chain for moving the telescopic column there is in principle the risk of a breakage and an uncontrolled lowering, i.e., extending, of the telescopic column. In this case there is an acute risk of injury or damage. In this respect a safety mechanism is to be provided that reliably stops movement in the case of a break.

It is therefore a further aspect of the present disclosure here to provide a simple and secure and relatively simply and compactly implementable solution.

In one embodiment of the disclosure a telescopic column comprising the following features is specified:
- at least two telescopic elements moveable linearly with respect to one another,
- at least one drive unit connected to a first of the telescopic elements,
- at least one connecting element, by which a force is transmissible from the drive unit to a second of the telescopic elements,
- a monitoring unit, which is configured such that an operating parameter of the connecting element is detectable,
- wherein upon detecting of the operating parameter outside of a predefinable range a defined change of an operating state of the drive unit is performable.

By monitoring the connecting element, a failure, wear, or generally a fault of the system can be reliably recognized in a simple manner, and the operating state of the drive unit adapted accordingly. A switching-off of the drive unit could be provided, for example, when the connecting element fails or a failure is imminent. For this purpose it is advantageous to also provide a locking mechanism, by which a further extending of the telescopic column is prevented. Alternatively or additionally an alarm can also be issued. Depending on the use case, for example, the existence of the connection of drive unit and second telescopic element can be monitored as state of the connecting element, depending on its specific embodiment. In the case of an embodiment of the connecting element as a cable, belt, or chain, it could thus be monitored whether the cable or belt or the chain is broken. Alternatively an aging condition and wear could be concluded from a stress of cable, belt, or chain so that the connecting element can be preventively exchanged.

In one preferred embodiment of the disclosure the telescopic column comprises a second drive unit and a second connecting element by which a force is transmissible from the second work unit to the second of the telescopic elements. Such a redundant drive system can also prevent an accident in the event of a total failure of the first connecting element and make possible the planned change of the operating state. Alternatively a further operation of the telescopic column can also be ensured. In this case an alarm is preferably additionally emitted.

In one preferred embodiment of the disclosure the monitoring device includes the following features:
- A detector element corresponding to at least one of the connecting elements and detecting its operating state,
- a switch element interacting with the detecting element, by which switch element a switching operation is performable, by which the operating state of at least one of the drive units is influenceable.

This design ensures in a simple manner that with detection of the state of the connecting element outside definable parameters the drive unit is switched off, for example, by a simple switching operation.

In one preferred embodiment of the disclosure the telescopic column further includes the following features:
- the detector element comprises a preloadable lever arm by which a defined clamping force is exertable on the connecting element,
- a counter-force element by which a counter-force is exertable on the connecting element,
- a basic tension of the connecting element, which basic tension is generated by a clamping force and counter-force, forms the operating parameter,
- the clamping force and the counter-force are chosen such that in the normal operating state of the connecting element a balance of the two forces prevails and the lever arm is held in a balance position,
- the connecting element is configured such that a change of the basic tension changes the balance such that the lever arm is deflectable out of its balance position,
- the switching element is configured such that with deflection of the lever arm out of its balance position the switching operation is performed.

Using this embodiment the state of a cable or belt or a chain can be mechanically and/or electronically monitored in a simple and reliable manner. In the case of a cable, with corresponding sensitivity an elongation caused by wear can also be detected and the cable exchanged prior to failure.

In one preferred embodiment of the disclosure the drive unit comprises a shaft on which the connecting element is disposed windable and unwindable, so that with winding or unwinding of the connecting element it is linearly movable with respect to the first telescopic element due to its connection to the second telescopic element. This embodiment is particularly compact and easy to manufacture, as well as particularly reliable.

In one preferred embodiment of the disclosure the connecting element is embodied such that with a failure of the connecting element the counter-force is fully or partially cancelled. This can be detected and evaluated in a particularly simple manner via a mechanical force meter as a change of the state of the connecting element.

The described aspects of the disclosure with reference to the drive system, the safety system, and the damping system can already in themselves bring significant advantages compared to known solutions. However, a particularly preferred embodiment of the disclosure comprises at least two of these systems, and in the ideal case, all three of these systems. Thus the drive system and the safety system according to embodiments of the disclosure work together and are optimally adapted to one another. The damping system likewise works together with the drive system in an adapted manner.

Further advantages, features and details of the invention arise from the exemplary embodiments of the disclosure described in the following with the assistance of the Figures.

BRIEF DESCRIPTION OF THE DRAWINGS

FIG. 12 shows a detail view of the coupling unit of FIG. 6, FIGS. 15 to 17 show the shock absorber according to FIG. 13 in a schematic sectional view in different operating states, FIGS. 20 to 24 show a monitoring unit for a telescopic column, FIGS. 25 to 27 schematically show the function of the monitoring unit.

DETAILED DESCRIPTION

Figure 1:
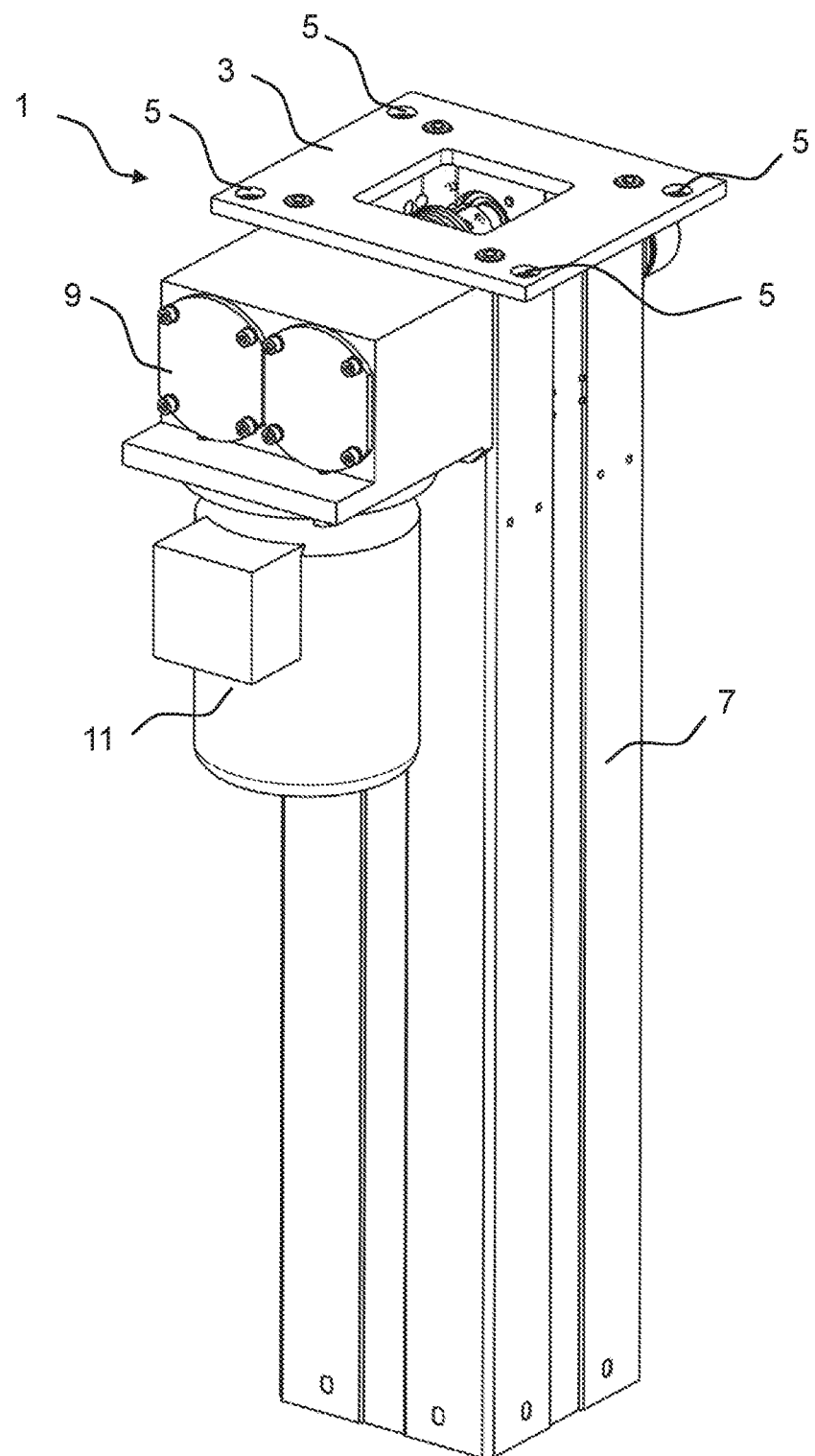
FIG. 1 shows telescopic column.

FIG. 1 shows a telescopic column in one embodiment as ceiling stand 1. A receiving plate 3 is disposed at its upper end, using which the ceiling stand 1 is attachable to the ceiling of a room via four screw holes 5. This can be, for example, a medical examination room, an operating room, a workshop, or a manufacturing device. A column element 7 is attached to the receiving plate 3, which column element 7 extends vertically downward in the installed state. Here the column element 7 is embodied nearly square with respect to its base area, with slightly chamfered edges. In other embodiments the base area can also have other geometries, i.e., for example, round or triangular. The base area can also change in the downward direction. A housing 9 is disposed laterally of the column element 7. The functional elements of a drive unit are disposed partially in the housing 9 and partially in the upper region of the column element 7. A motor 11 is disposed below the housing 9 that is designed to interact with the elements of the drive unit. The internal design of the drive unit is described in detail with reference to FIGS. 4 and 5.

Alternatively such embodiments are also possible for telescopic columns that are designed to stand on the floor. In this case the outermost, in other embodiments also the innermost column element is attached to the floor or to a movable or moving frame, and with actuation of the drive unit the inner- or outer-lying column elements are extended upward or retracted downward.

Figure 2:
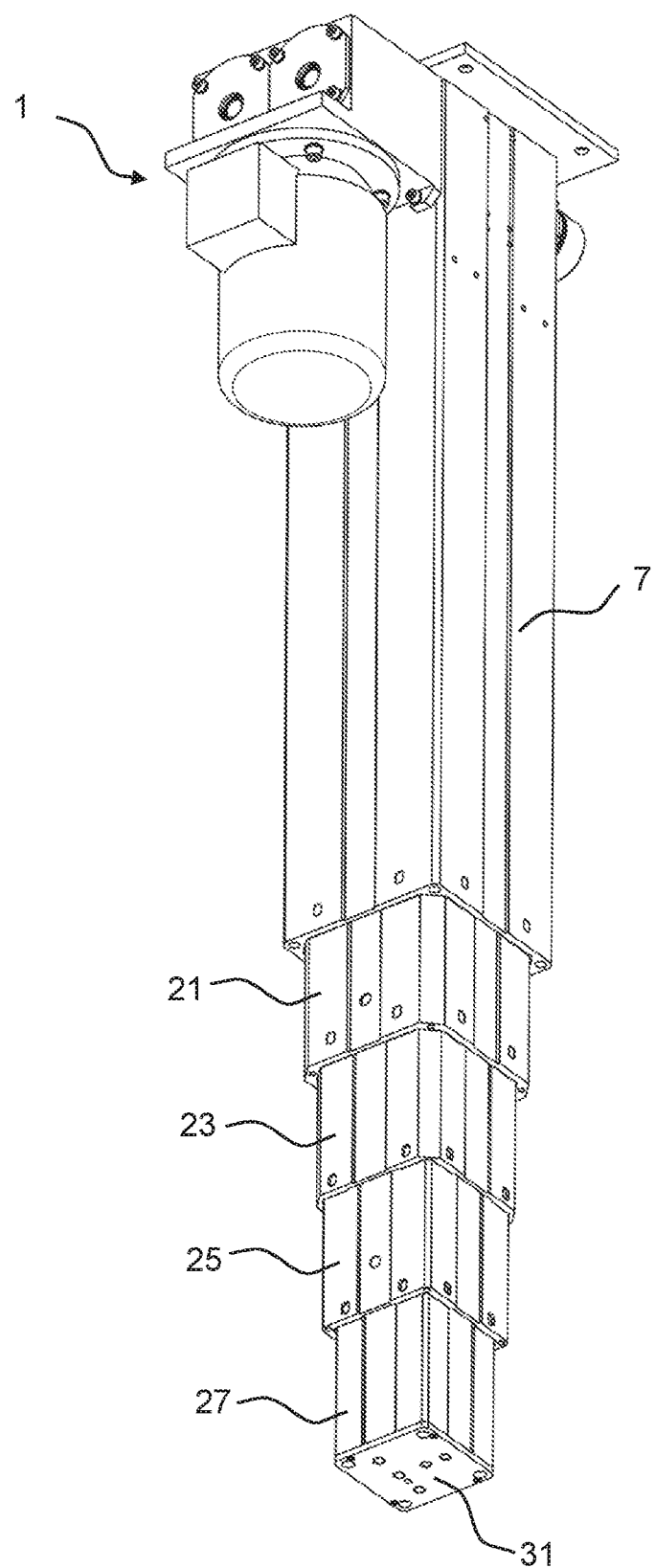
FIG. 2 shows the telescopic column in a partially extended state.

In FIG. 2 the ceiling stand 1 is depicted in another operating state. Inside the column element 7 four further column elements 21, 23, 25 and 27 are disposed one-inside-the-other. The size of each base area respectively decreases here so that the column element 27 has the smallest base area. The four column elements 21, 23, 25, and 27 are linearly movable with respect to the respective directly farther-outer-lying column element 7, 21, 23, or 25. Thus the column element 21 can move downward out of the column element 7. Analogously the column element 23 can move linearly downward out of the column element 21, etc. a receiving plate 31 is disposed at the lower end of the column element 27 on which a load to be lifted or lowered can be attached. Alternatively the load can also be directly connected through the receiving plate to the column element 27. The load can be, for example, an X-ray apparatus. The drive unit and the motor 11 can be controlled via a not-depicted operating unit, which is embodied, for example, as a remote control or handle, and thus extend the column elements 21, 23, 25, and 27 downward and retract them upward. Accordingly the attached load is raised or lowered.

Figure 3:
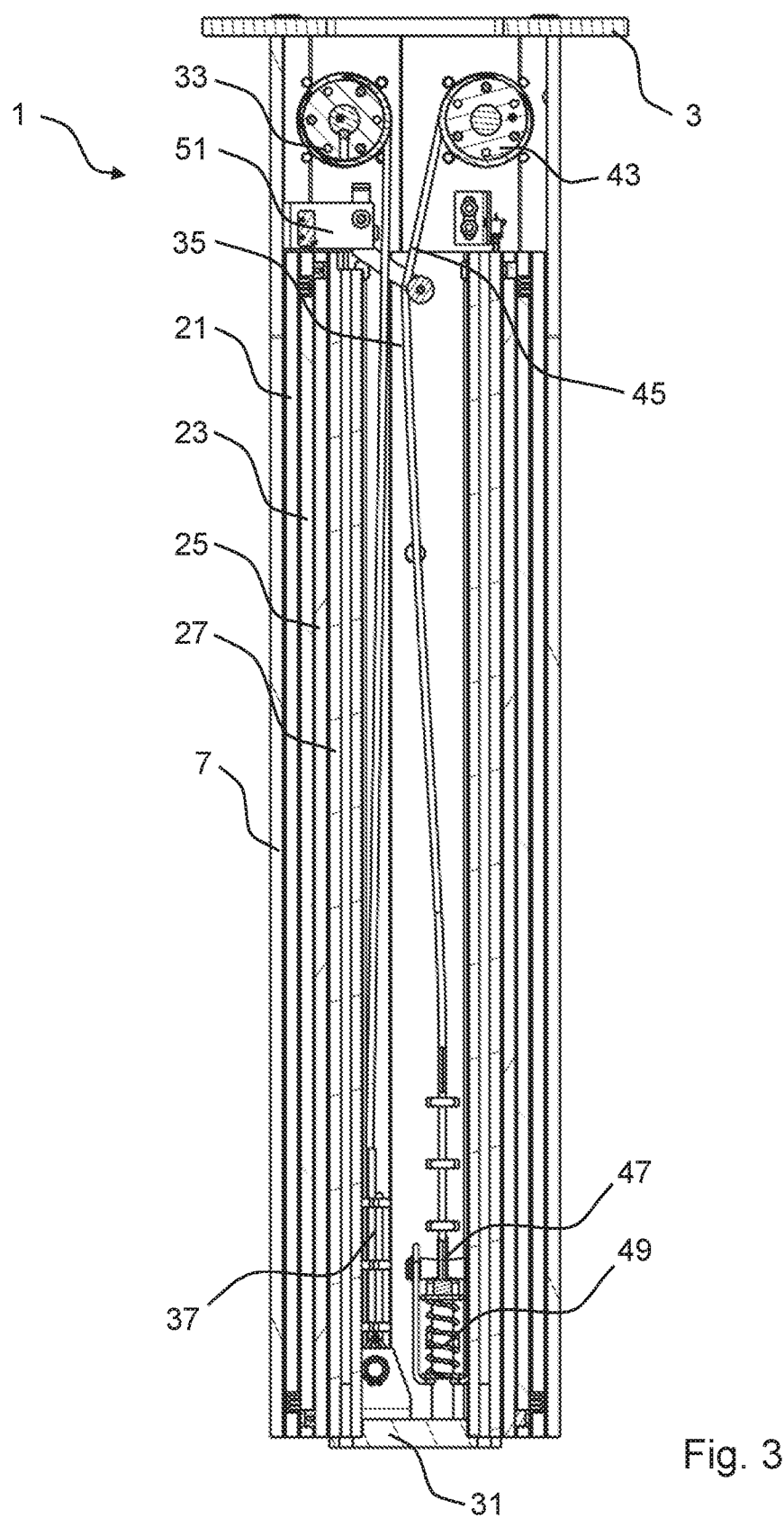
FIG. 3 shows a sectional view of the telescopic column according to FIG. 1.

FIG. 3 is a sectional view of the ceiling stand 1. Inside the column element 7, attached under the receiving plate 3, four further column elements 21, 23, 25, and 27 are depicted in the retracted state. A part of the drive unit is supported above the four column elements 21, 23, 25 and 27 in the column element 7. The drive unit comprises a first cable drum 33 rotatably supported in the housing, on which cable drum 33 a cable 35 is wound. The cable 35 is connected to the receiving plate 31 on the other end by an attachment unit 37. By rotating the cable drum 33, in this depiction in the clockwise direction, the cable 35 is unwound from the cable drum 33, whereby the column element 27, and subsequently the column elements 21, 23, and 25 continually lower due to gravity. Depending on the friction conditions present or the construction the lowering can also occur discontinuously, perhaps by the column elements 21, 23, 25, and 27 extending sequentially. In this way the ceiling stand 1 can extend downward and lower the attached load. By rotating the cable drum 33 in the counterclockwise direction an upwardly directed force is exerted on the receiving plate 31 so that the column elements 21, 23, 25 and 27 retract again.

In the depicted embodiment according to the disclosure a further cable drum 43 is provided on which a cable 45 is wound. The cable 45 is in turn connected via an attachment unit 47, and this via a spring 49, to the receiving plate 31. The spring serves to relieve the cable 45 if different speeds of the cables 35 and 45 arise in operation due to tolerance differences or expansions of the components. With respect to the direction of rotation, the cable 45 is wound around the cable drum 43 differently than the cable 35, so that with counterclockwise rotation of the cable drum 43 it is unwound and with clockwise rotation it is wound. To lower the support plate 31 and thus to extend the ceiling stand 1 it is consequently necessary that according to the depiction of FIG. 3 the cable drum 33 and the cable drum 43 are simultaneously rotated clockwise and counterclockwise respectively. Accordingly to retract the ceiling stand 1 the cable drum must be rotated counterclockwise and the cable drum 43 rotated clockwise. The cable drum 43 and the cable 45 wound onto it serve mainly as a redundant safety mechanism in case the cable 35 wears or breaks during use. In this case the receiving plate 31 and thus the column elements 21, 23, 25, and 27 would be held by the cable 45 and also be movable further.

The ceiling stand 1 further includes a monitoring unit 51, whose structure and function is described in detail with reference to FIGS. 20 to 27.

Figure 4:
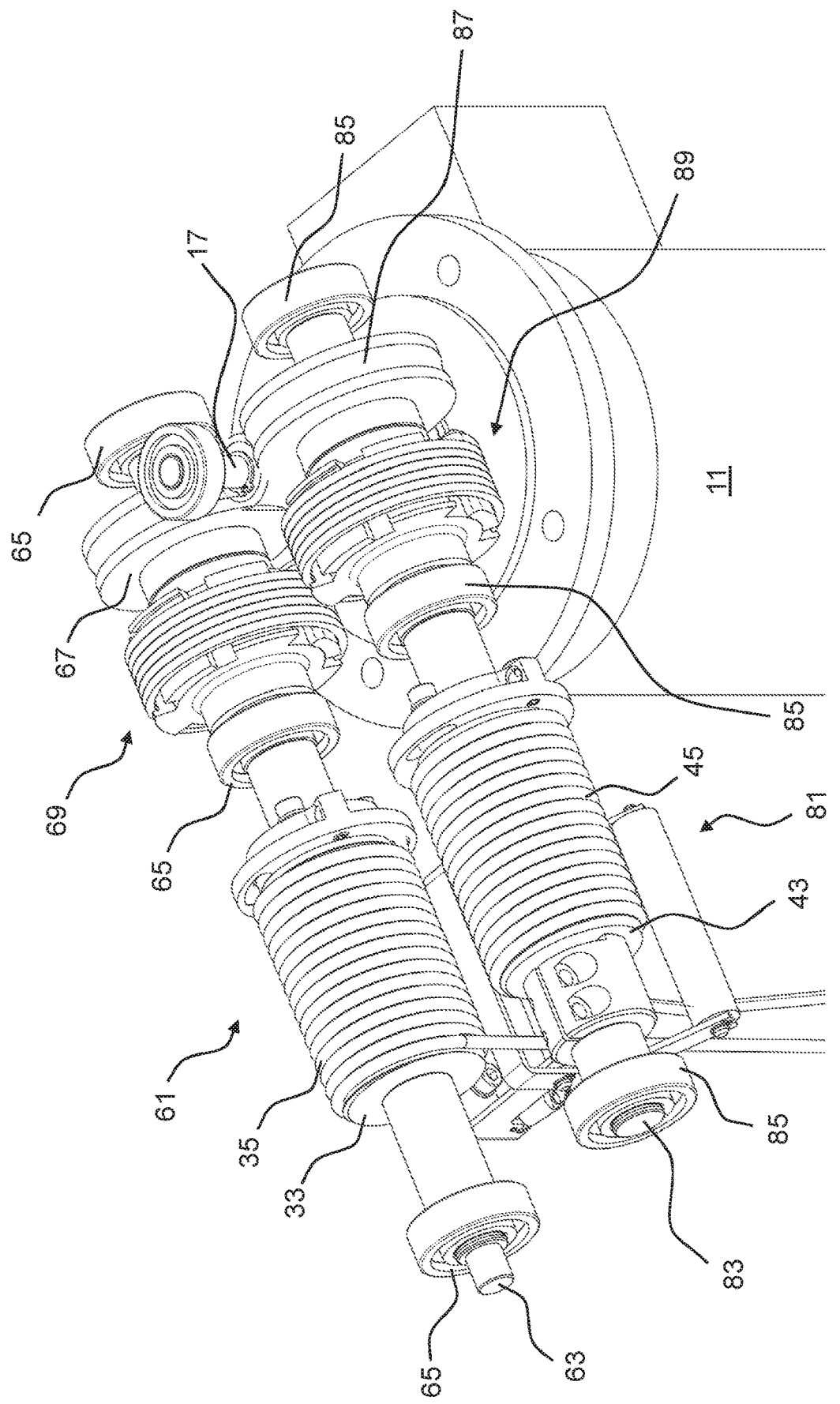
FIG. 4 shows a detail view of a drive unit of the telescopic column according to FIG. 1.

In FIG. 4 essential parts of the drive unit are depicted in section. The drive unit comprises a main drive unit 61 as well as a safety unit 81. The main drive unit 61 includes a shaft 63, which is supported via three bearing points 65 in the drive housing 9 (not depicted) or in the column element 7. On the shaft 63 the cable drum 33 is attached to the cable 35. Drive-side the main drive unit 61 includes a worm gear 67 that can be set into rotational movement via a drive shaft 17 of the motor 11. The worm gear 67 is radially and axially defined; however, it can rotate about the shaft 63. The force transmission between the worm gear 67 and the shaft 63 is effected via a coupling unit 69 whose function is described in detail with respect to FIGS. 5 to 12.

The safety unit 81 is constructed analogously to the main drive unit 61. It also comprises a shaft 83 that is supported via three bearings 85. On the shaft 83 the cable drum 43 is attached to the cable 45. Also analogously a worm gear 87 is provided that is also in engagement with the drive shaft 17. Due to the opposite arrangement of the two worm gears 67 and 87 with respect to the drive shaft 17, it is ensured that with rotation of the drive shaft 17 the two worm gears 67 and 87 each rotate in opposite directions. Due to the opposing winding directions of the two cables 35 and 45, with rotation of the drive shaft 17 in one direction both cables 35 and 45 are unwound, and with opposite rotation wound up. Also with the safety unit 81 the force transfer between the worm gear 87 and the shaft 83 is effected via a coupling unit 89 that is constructed analogously to the coupling unit 69.

Figure 5:
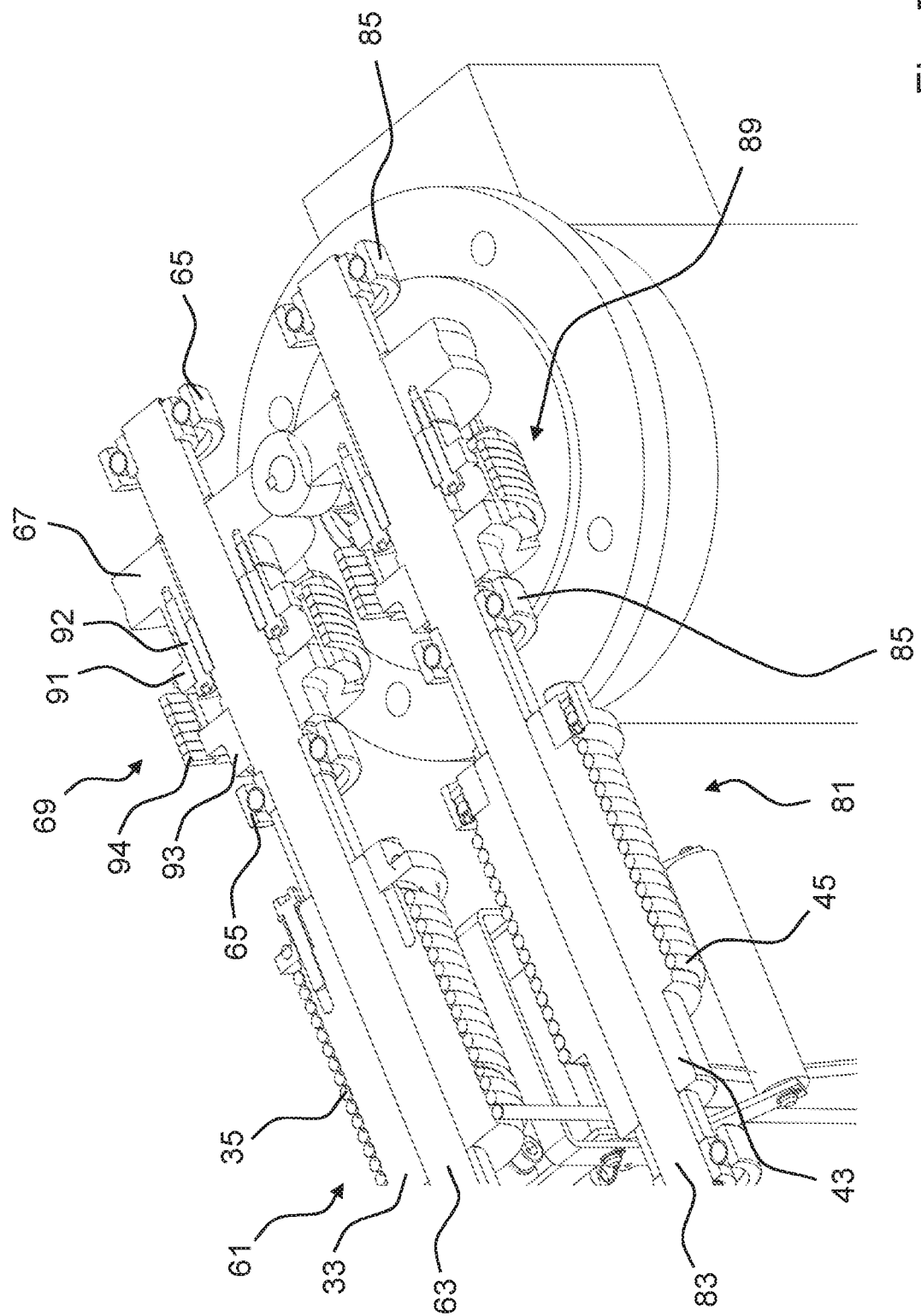
FIG. 5 shows a sectional view of the drive unit according to FIG. 4.

In FIG. 5 a sectional view of the drive unit is depicted. The shafts 63 and 83 of the main drive unit 61 and of the safety unit 81 are depicted. A renewed explanation of the elements already described with respect to FIG. 4 is omitted here; rather, the mode of action of the coupling units 69 and 89 shall be described. The inner diameters of the worm gears 67 and 69 are larger than the outer diameter of the shafts 63 and 83, respectively. In this respect a rotational movement of the worm gears 67 and 69 is not transmitted to the shafts 63 and 83 by a direct contact. The transmission of the force is exemplarily explained on the basis of the coupling unit 69. The coupling unit 89 functions analogously.

Drive-side the coupling unit 69 comprises a first clutch element 91 that is fixedly connected to the worm gear via screws 92, and pins (not depicted). The clutch element 91 also has a larger inner diameter than the outer diameter of the shaft 63, so that also here no direct torque transfer to the shaft 63 takes place. Output-side the coupling unit 69 includes a second clutch element 93 that is disposed axially opposing the clutch element 91. At its inner diameter the clutch element 93 is disposed on the shaft 63 in a fixedly seating manner A rotational movement of the clutch element 93 consequently exerts a torque on the shaft 63, by which the shaft 63 is also set into rotation in the same direction. A rotational movement of the shaft 63 generated output-side also exerts a torque on the coupling unit 93. The coupling unit 69 further includes a coil spring 94 that serves as a retaining mechanism. The detailed design and the mode of action of the coupling unit 69 is described in detail in FIGS. 6 to 12.

Figure 6:
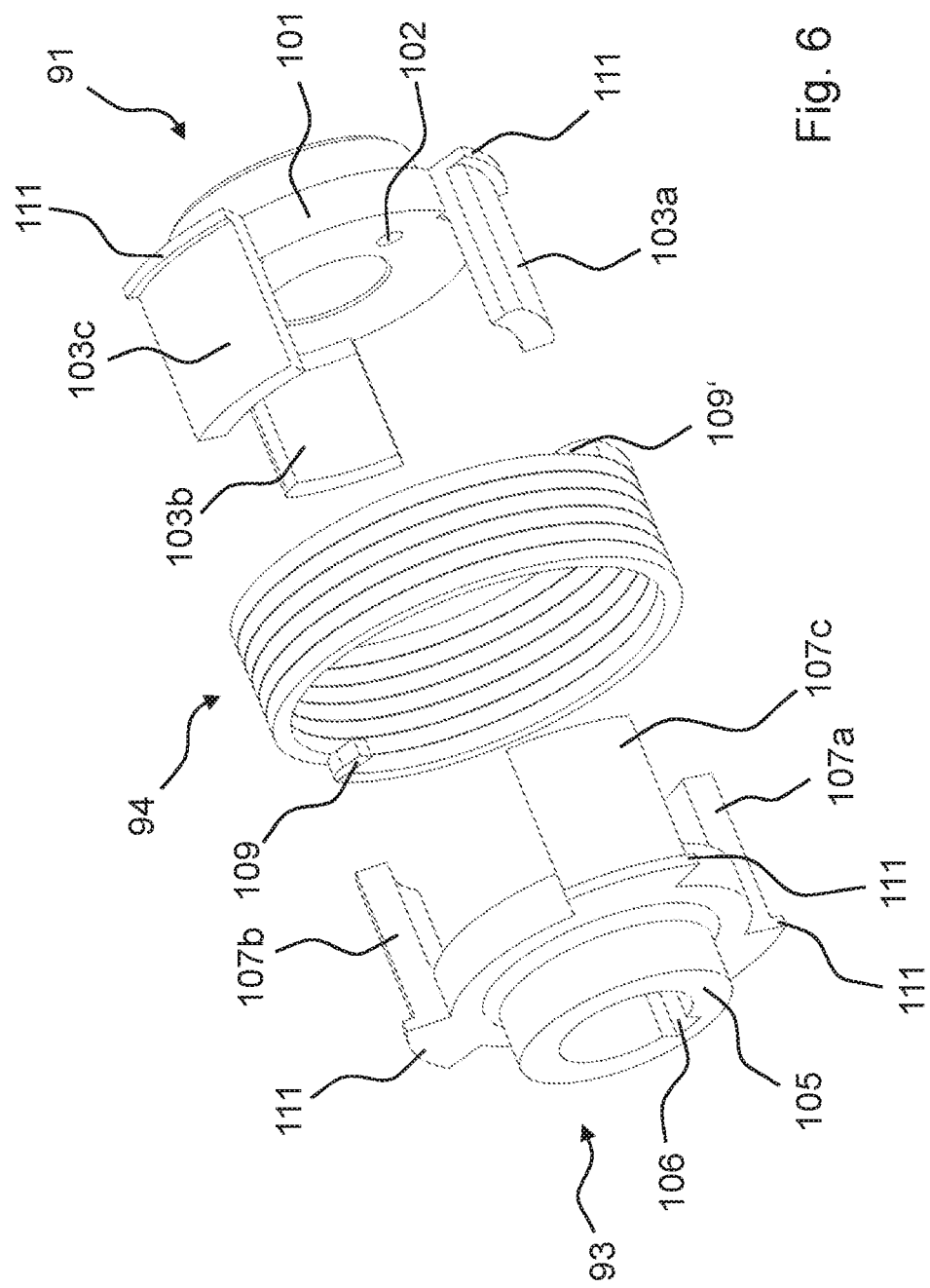
FIG. 6 shows an exploded view of the coupling unit of the drive unit according to FIG. 4.

In FIG. 6 the two clutch elements 91 and 93, as well as the coil spring 94, are depicted pulled apart axially in an exploded view. The clutch element 91 includes a ring-type base element 101 in which screw holes 102 are provided for receiving the screws 92 not depicted here (see FIG. 5) and/or pins. Radially outward on the base element 101 three claw-type coupling elements 103a, 103b, and 103c are disposed that extend axially toward the clutch element 93. The clutch element 93 includes a shaft seat 105 that resembles the base element 101 with respect to its external design. However, at the inner diameter the shaft seat 105 is adapted to the diameter of the shaft 63 or 83 such that after the installation there is a friction-fit or keyed connection. For this purpose at its inner diameter the shaft seat 105 includes an axially extending groove 106 that is in engagement with a corresponding projection on the shaft 63 or 83 or a key and supports the coupling for conjoint rotation. In comparison thereto the base element 101 sits in contrast only loosely on the shaft 63 or 83; it is thus not connected thereto such that they rotate together. Radially outwardly lying the clutch element 93 includes three claw-type coupling elements 107a, 107b, and 107c that extend axially toward the clutch element 91.

The coupling elements 103a, 103b, and 103c and 107a, 107b, and 107c can be considered as sections of a cylindrical shell; thus they have a curved configuration in the circumferential direction. With respect to their dimensions they are chosen small in the circumferential direction such that a relatively large spacing respectively remains between them. With axial joining of the two clutch elements 91 and 93, each one of the coupling elements 103a, 103b, and 103c comes to rest between two of the coupling elements 107a, 107b, and 107c. Analogously each one of the coupling elements 107a, 107b, and 107c lies between two of the coupling elements 103a, 103b, and 103c. End-side the coupling elements 103a, 103b, and 103c then lie slightly radially spaced outside the outer circumference of the shaft seat 105. Analogously the coupling elements 107a, 107b, and 107c lie slightly radially spaced outside the outer circumference of the base element 101. The clutch elements 103a, 103b, and 103c and 107a, 107b, and 107c are also chosen small with respect to their dimensions in the circumferential direction such that there is a defined distance respectively between one of the coupling elements 103a, 103b, and 103c and the adjacent two coupling elements 107a, 107b, and 107c, i.e., even in the assembled form a complete cylindrical shell is not formed. Thus, for example, with initially central orientation of the coupling elements 103a, 103b, and 103c and 107a, 107b, and 107c with respect to one another the clutch element 93 can be rotated about a defined angle until it comes into contact with another of the components.

Radially outside the coupling elements 103a, 103b, and 103c and 107a, 107b, and 107c the helically shaped coil spring 94 wraps around these. End-side the coil spring 94 respectively includes radially inwardly curved ends 109 (output side) and 109' (drive side) on which each one of the coupling elements 103a and 103b or 107b and 107c can exert a force acting on the coil spring 94 in the circumferential direction. The end 109 lies between the coupling elements 103b and 107b; thus depending on the rotation direction it can enter into operative contact with these. The end 109' lies between the coupling elements 103a and 107c and can enter into operative contact with these in an analogous manner Due to their arrangement the coupling elements 103c and 107a do not enter into contact with the ends 109 and 109' in any operating state. For axial fixing of the coil spring 94, the coupling elements 103a, 103b, and 103c and 107a, 107b, and 107c each include an end-side, radially outer-lying projection 111.

Figure 7:
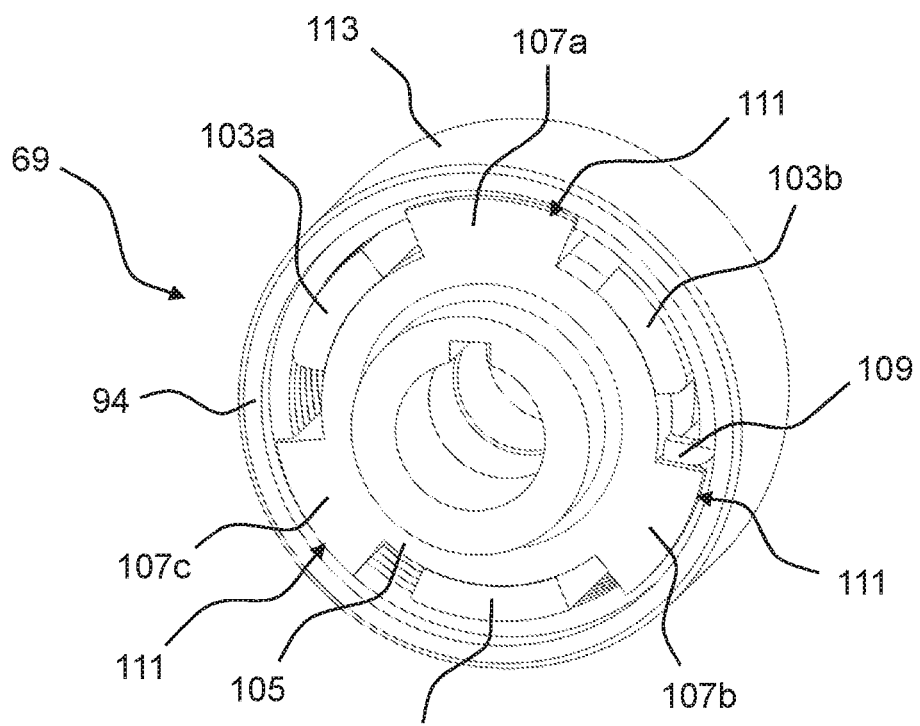
FIG. 7 shows the coupling unit of FIG. 6 from the viewing direction of the output side.

In FIG. 7 the coupling unit 69 is shown in a three-dimensional depiction in the assembled state from the viewing direction of the output side. The outer part of the coupling unit 69 comprises a brake housing 113, which is attached in the housing of the ceiling stand 1 such that it is secured against rotation. In each of the depictions of FIGS. 4, 5 and 6 the brake housing has not been shown for better overview. In FIG. 7 it can be seen how the coupling elements 103a, 103b, and 103c lie end-side outside the outer circumference of the shaft seat 105, and due to the distance of the clutch elements 103a, 103b, and 103c and 107a, 107b, and 107c a limited, independent rotation of the clutch elements 91 and 93 with respect to each other is possible.

The coil spring 94 is wound and dimensioned such that with installation in the brake housing 113 it must be radially contracted, i.e. radially reduced. The coil spring 94 is held under tension radially by the brake housing 113 and axially by the projections 111, so that the coil spring 94 cannot directly relax again and is held in the preloaded state. In this state the coil spring 94 is therefore not rotatable in the brake housing 113 and develops a defined retaining force depending on the design. The clutch element 93 is rotatable about a small angle until, depending on the direction of rotation, either the coupling element 107b presses against the end 109 (as depicted in FIG. 7) or the coupling element 107c presses against the end 109' (see FIG. 8). The end 109 of the coil spring 94 lies between coupling elements 103b and 107b.

Figure 8:
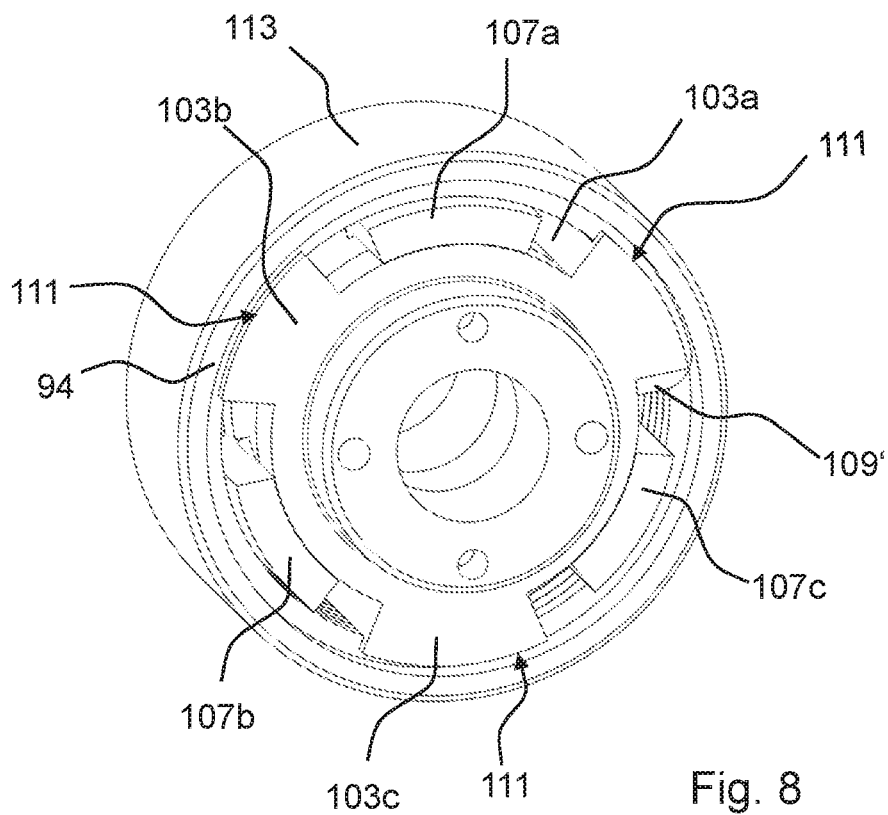
FIG. 8 shows the coupling unit of FIG. 6 from the viewing direction of the drive side.

In FIG. 8 the coupling unit 69 is depicted in a depiction analogous to FIG. 7, but here from the viewing direction of the drive side. Here it can analogously be seen how the coil spring 94 is held axially by the projections 111 and is thus axially fixed overall. The second end 109' of the coil spring 94 lies between the coupling elements 103a and 107c.

After installation of the coupling unit 69 or 89 on the shaft 63 or 83 and the receiving of the load, due to the gravitational force an output-side torque generated by the column elements 21, 23, 25 and 27 via the cables 35 and 45 and the cable drums 33 and 43 permanently acts on the respective coupling element 93. This is then rotated in a manner depending on the direction of rotation so far until either the coupling element 107b presses against the end 109 or the couple element 107c presses against the end 109'. The respective end 109 or 109' consequently receives a force acting in the circumferential direction. Due to the winding direction of the coil spring 94, in both cases this force effects a force on the coil spring 94, since this tries to widen. Due to the surrounding brake housing 113 the force causes no actual widening, but rather a strengthening of the frictional operative contact of the coil spring 94 with the brake housing 113. Due to the initial retaining force due to the preload and this increased friction, the output-side torque is fully compensated and a further rotating is prevented. An unwinding of the coil 35 or 45 and an extending of the column elements 21, 23, 25 and 27 is thus prevented; the arrangement consequently retained. This is the initial state of the ceiling stand 1. An increase of the output-side torque, for example, by enlarging of the received load, increases the pressure on the coil spring 94 and thus the friction with the brake housing 113 so that even then the position is held.

Figure 9:
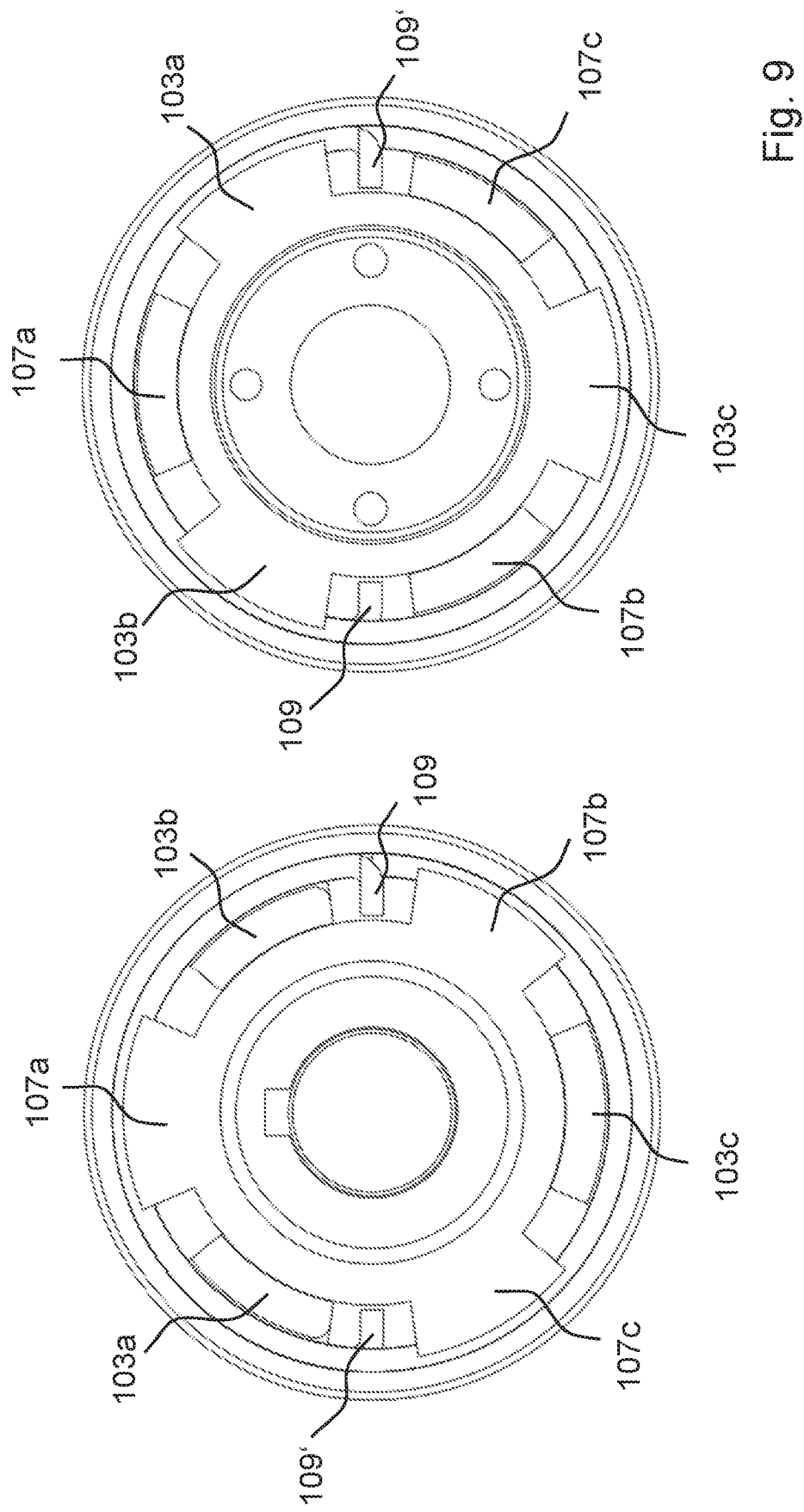
FIGS. 9 to 11 show the coupling unit of FIG. 6 from both viewing directions in different operating states.
Figure 10:
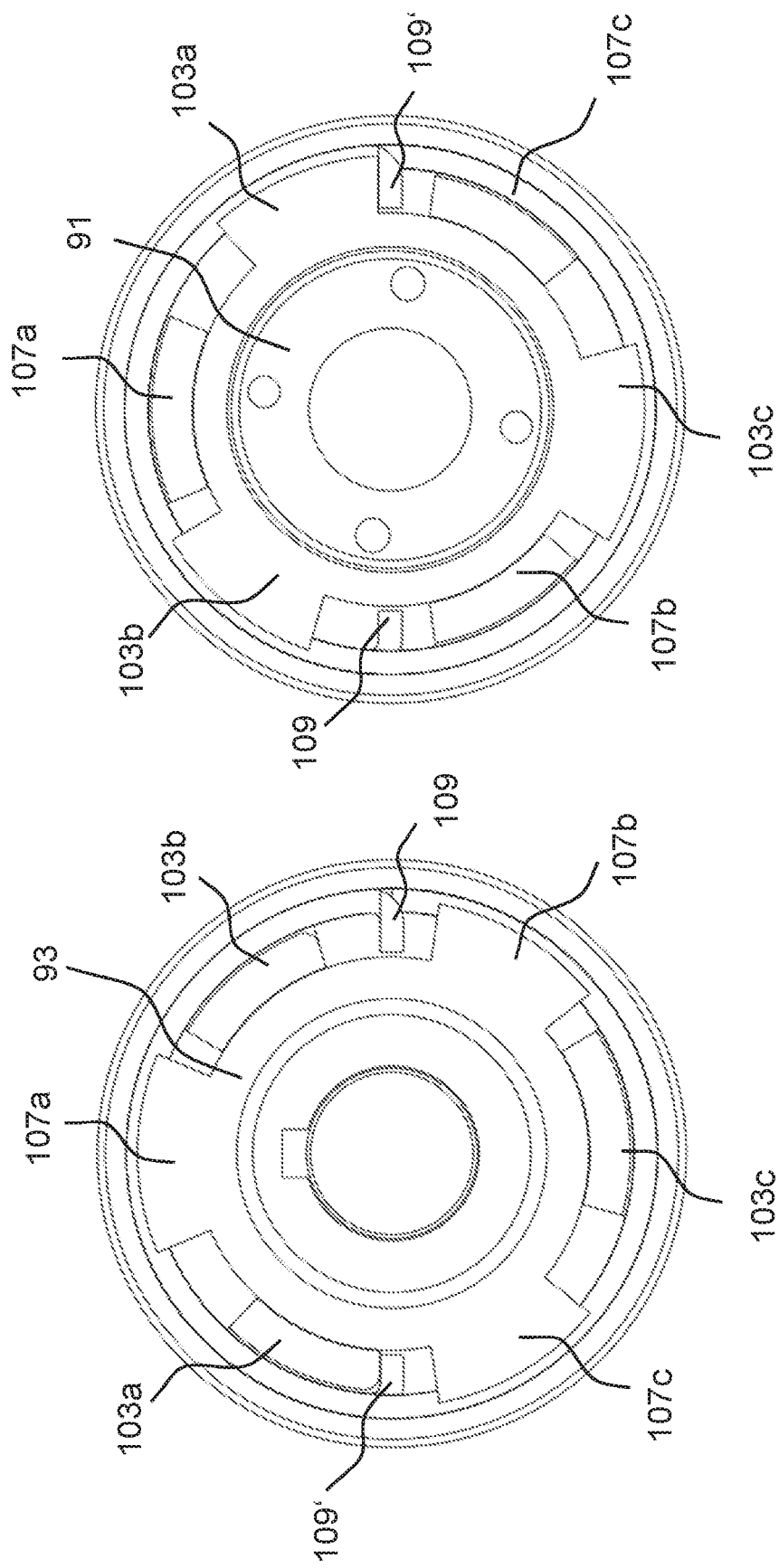
Figure 11:
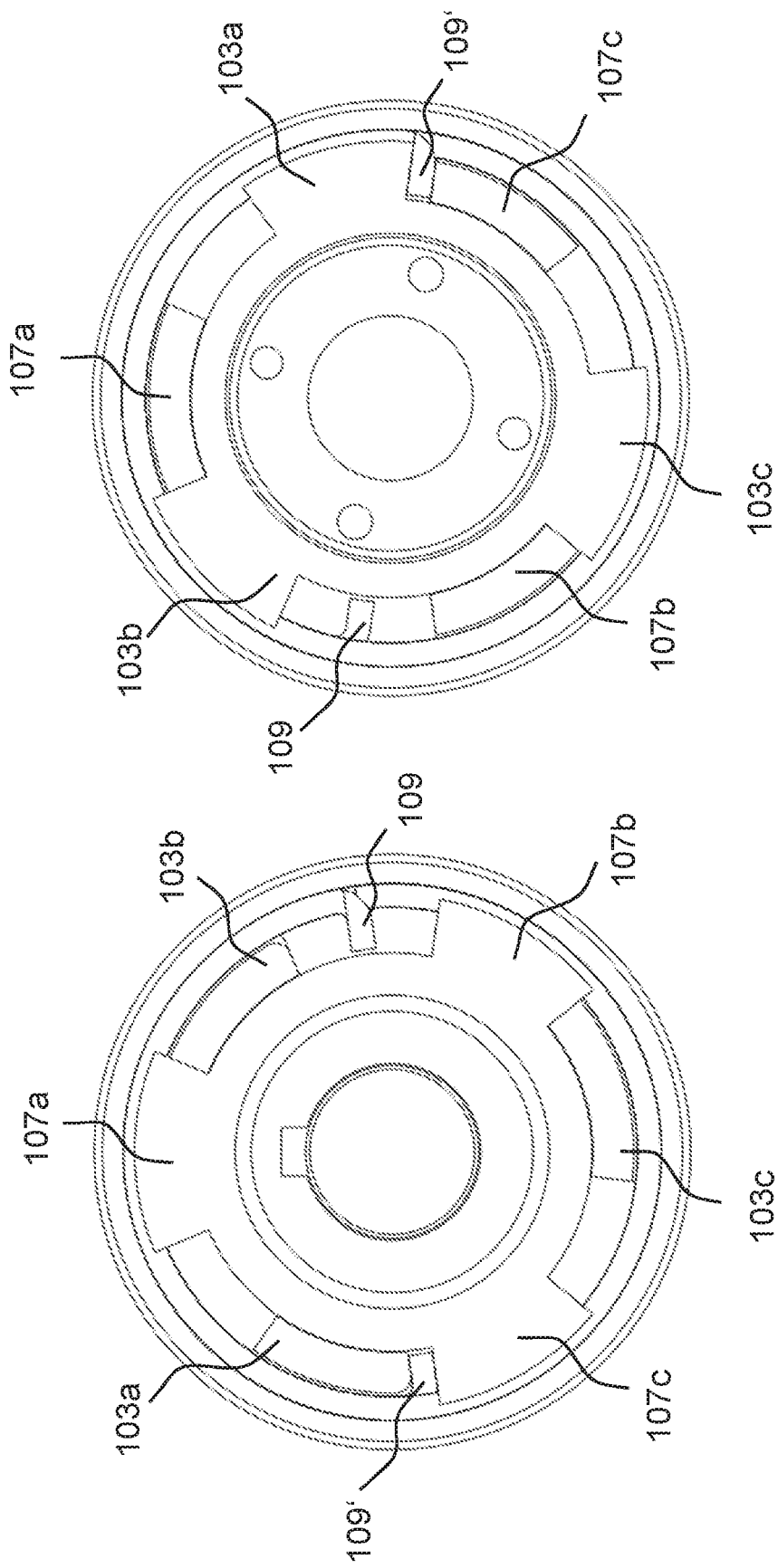

In FIGS. 9, 10, and 11 the coupling unit 69 is depicted in various operating states, each from the viewing direction of the output side (left) and of the drive side (right). Here the position of the coupling elements 103a, 103b, and 103c or 107a, 107b, and 107c with respect to the ends 109 and 109' is different.

In FIG. 9 an intermediate state is depicted wherein none of the coupling elements 103a, 103b, and 103c or 107a, 107b, and 107c are in contact with the ends 109 and 109'. Accordingly the end 109 lies free between the coupling elements 103b and 107b. The end 109' lies free between the coupling elements 103a and 107c.

In FIG. 10 after a rotating of the drive-side clutch element 91 the coupling element 103a is in contact with the end 109'. With a continuing of the rotation in the same direction the coupling element 103a will exert a force on the end 109' and move it in the clockwise direction (right depiction). The coil spring 94 is thus radially contracted, and the retaining force with respect to the brake housing 113 is reduced. After brief further turning the end 109' enters into contact with the coupling element 107c, which is depicted in FIG. 11. The clutch element 93 is then moved along in the same direction. This rotating is then transmitted to the cable drum 33 or 43 and correspondingly the cables 35 or 45 are wound or unwound. Depending on the direction of rotation a retracting or extending of the ceiling stand 1 thus results.

In order that the transfer of the drive torque does not only take place via the contact between the coupling element 103a, the end 109', and the coupling element 107c, the dimensions of the components in the circumferential direction are chosen such that with the production of this effect chain the coupling elements 107b and 103 are also in contact by their mutually facing side surfaces and additionally transfer the drive torque. The end 109' is consequently relieved.

In FIG. 12 the size ratios are illustrated schematically. The coupling elements 103a, 103b, 107b and 107c each span an angle γ, the coupling elements 107a and 103c an angle β. An angle α falls between the coupling elements 107a and 107b or 107c. The same angle α falls between the coupling elements 103c and 103a or 103b. The sizes of the angles α, β and γ are chosen such that the coupling elements 107b and 103c enter into contact simultaneously when the couple element 103a enters into contact with the end 109' and the end 109' enters into contact with the coupling element 107c. A reliable torque transmission is thus ensured.

A drive-side rotating of the clutch element 93 in the other direction of rotation works in a completely analogous manner, wherein the end 109 then forms an effect chain with the coupling elements 103b and 107b, and the coupling elements 103c and 107c are in direct operative contact. The ceiling stand 1 is extended or retracted accordingly.

With a rotating of the drive shaft of the motor 11, the worm gear 67 coupled thereto receives a torque and set into rotation. This is transmitted by the screw connection to the clutch element 91. With a rotating in the clockwise direction from the viewing direction of the drive side as in FIG. 8, for example, the coupling elements 103a, 103b, and 103c rotate in the clockwise direction toward the coupling elements 107a, 107b, and 107c, and here the space located between them initially decreases. Here an increased pressure results of the coupling element 103a with the end 109' of the coil spring 94. Due to the built-up pressure on the end 109' of the coil spring 94 is subjected to a force acting in the circumferential direction in the clockwise direction. With sufficiently large drive-side torque a radial contracting of the coil spring 94 results, so that the friction-fit connection to the brake housing 113 is relaxed. Consequently the output-side torque is no longer completely compensated, with the result that the shaft is set into rotation and the cable 35 or 45 unwinds and the column elements 21, 23, 25, and 27 are extended. This leads to a lowering of the load. Due to the existing output-side torque the coupling element 107c remains in constant contact with the end 109' of the coil spring 94; it is thus also rotated along in the clockwise direction. As soon as the drive-side torque is omitted due stoppage of the rotational movement of the motor 11, the then no longer compensated or overcompensated output-side torque immediately leads to a widening of the coil spring 94 again and a friction-fit contact with the brake housing 113 and thus production of the retaining force, with the result that the load is held at the new level.

With a rotating of the worm gear 67 and thus of the coupling element 91 in the counterclockwise direction, a convergence of the coupling elements 103a, 103b, and 103c and 107a, 107b, and 107c analogously results. In this case the coupling element 103b interacts with the end 109 of the coil spring 94 and the coupling element 107c with the end 109' of the coil spring 94 in an analogous manner, with the result that the rotational movement is in turn transmitted to the shaft 63. In this case the cable 35 is wound and the load is lifted.

In a fully analogous manner the coupling unit 89 acts between worm gear 87 and shaft 83. Due to the construction of the coupling unit 69 or 89 it does not matter in which direction of rotation the torques each act. A drive-side torque always leads to a contracting of the coil spring 94 and a loosening of the brake, while an output-side torque widens the coil spring 94 and increases the brake effect.

Figure 13:
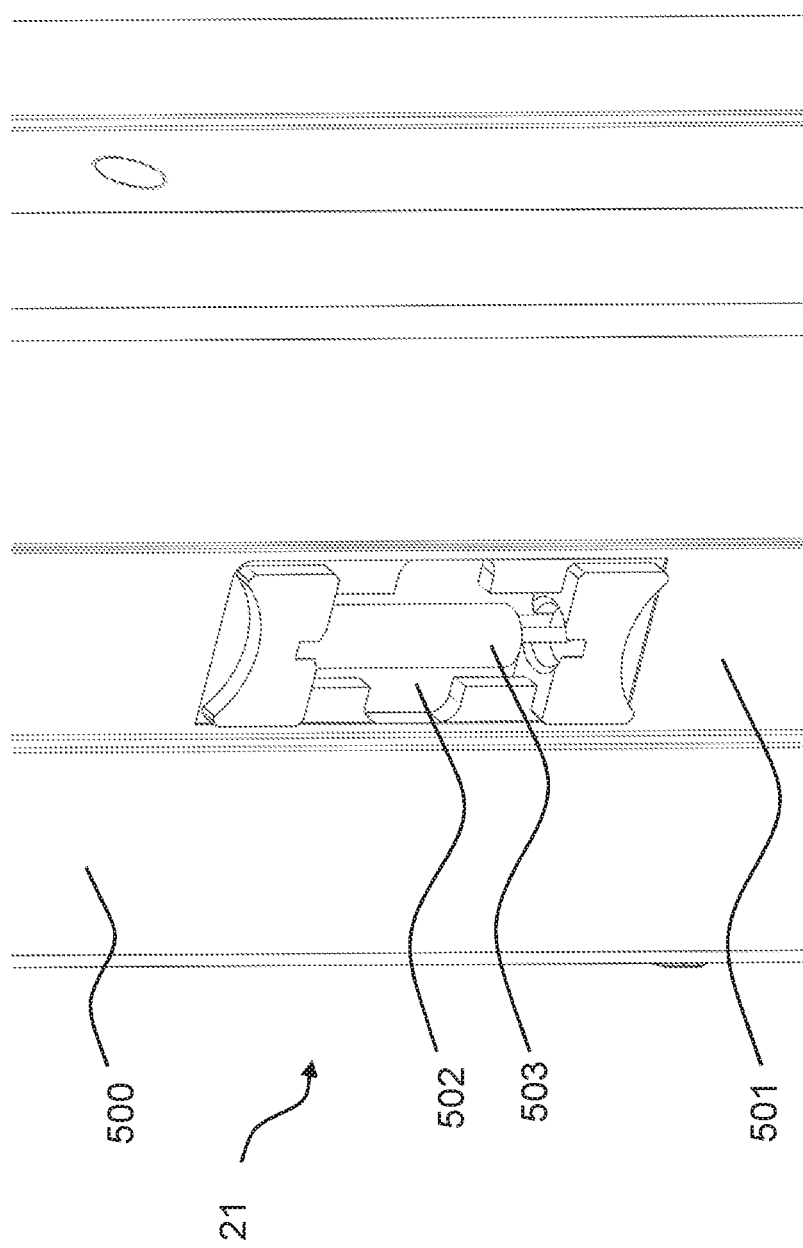
FIG. 13 shows a shock absorber for a telescopic column.

In FIG. 13 one of the column elements 21 is sectionally depicted. The other column elements 23, 25 and 27 are analogously constructed. On a side surface 500 it includes a flat and wide groove-shaped recess 501, wherein a slot 502 is formed. A shock absorber 503 is inserted and secured in the slot 502. The construction of the shock absorber 503 is described in detail in FIGS. 14 to 17, its mode of operation on the basis of FIGS. 18 and 19.

Figure 14:
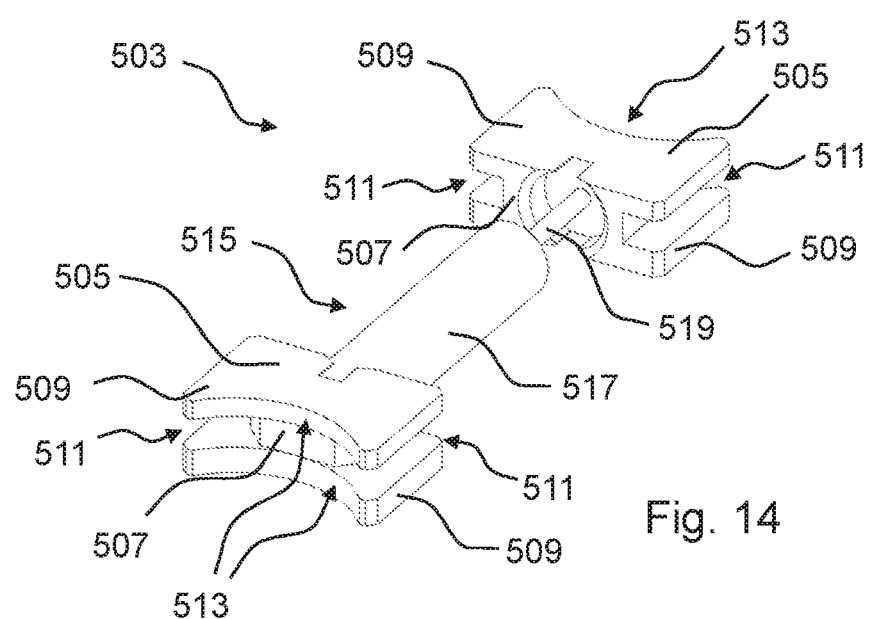
FIG. 14 shows the shock absorber according to FIG. 13 in a detail view.

In FIG. 14 the shock absorber 503 is depicted. It includes a receiving element 505 on each end side, each of which receiving elements 505 includes a center part 507 and two guide parts 509. The guide parts 509 are wider than the center part 507, so that a groove 511 arises laterally in each case. In the installed state, the housing of the column element 21, which housing borders the slot 502, engages into the grooves 511, with the result that the shock absorbers 503 are secured and guided. End-side the guide parts 509 have a round shape 513. Between the center parts 507 a damping element 515 is disposed that comprises a cylinder 517 and a plunger 519. With exerting of axial pressure on the plunger 519 and the cylinder 517 the plunger 519 enters the cylinder 517 in a damped manner Thus the spacing of the two center parts 517 can decrease. With decreasing spacing the force to be expended is greater due to the damping properties of the damping element 515, until the plunger 519 is completely received in the cylinder 517. The damping element 515 can be embodied, for example, as is known from drawer- or door-dampers. As can be seen in FIG. 13 the width of the slot 502 is not constant over its length, but rather is wider in the center. The central width is chosen such that the guide parts 509 are completely received there and can be successively pushed toward the axial end of the slot 502 so that the housing can engage into the grooves 511 and the shock absorber is secured. For installation it is necessary to axially compress the shock absorber 503 so that the second guide part 509 is placed in the wide part of the slot and can then be pushed to the axial end by relaxing of the shock absorber 503.

In FIGS. 15 to 17 the inner construction of the shock absorber is schematically depicted. The cylinder 517 is filled with a liquid 521. Alternatively a gas can be used. Furthermore in the cylinder 517 a spring 523 is disposed that presses a piston 525 upward. The piston 525 is in turn connected to the plunger 519; it can thus be acted upon with a force. The piston 525 can move against the force of the spring 523 in the cylinder 517. The piston 525 comprises a channel 527, through which during movement the liquid 521 can flow between the two half-spaces of the cylinder 517, which half-spaces are defined by the piston 525. Otherwise the piston 525 would be blocked due to the incompressible liquid 521. The piston 525 comprises a further channel 529 that is embodied significantly wider than the channel 527. The channel 529 is provided with a valve 531 that makes possible a passage of liquid 521 only in a movement direction of the piston 525, namely with an upward-directed movement.

In FIG. 16 due to an impinging of the plunger 519 with a force the piston is moved upward, whereby the spring 523 is compressed. Due to the relatively narrow channel 527 a flow specifically of the liquid 521 is made possible, but the upward movement of the piston 525 is strongly damped and thus slowed. The kinetic energy is correspondingly absorbed. The valve 531 is closed, with the result that no liquid 521 can flow through the channel 529.

In FIG. 17 the plunger 519 is no longer acted upon by a force, with the result that the piston 525 is moved upward again by the spring 523 into its initial position. In this movement direction the valve 531 opens and the liquid 521 can flow through the channels 527 and 529. The upward-directed movement of the piston 525 is therefore significantly less strongly damped than the previous downward-directed movement.

Figure 19:
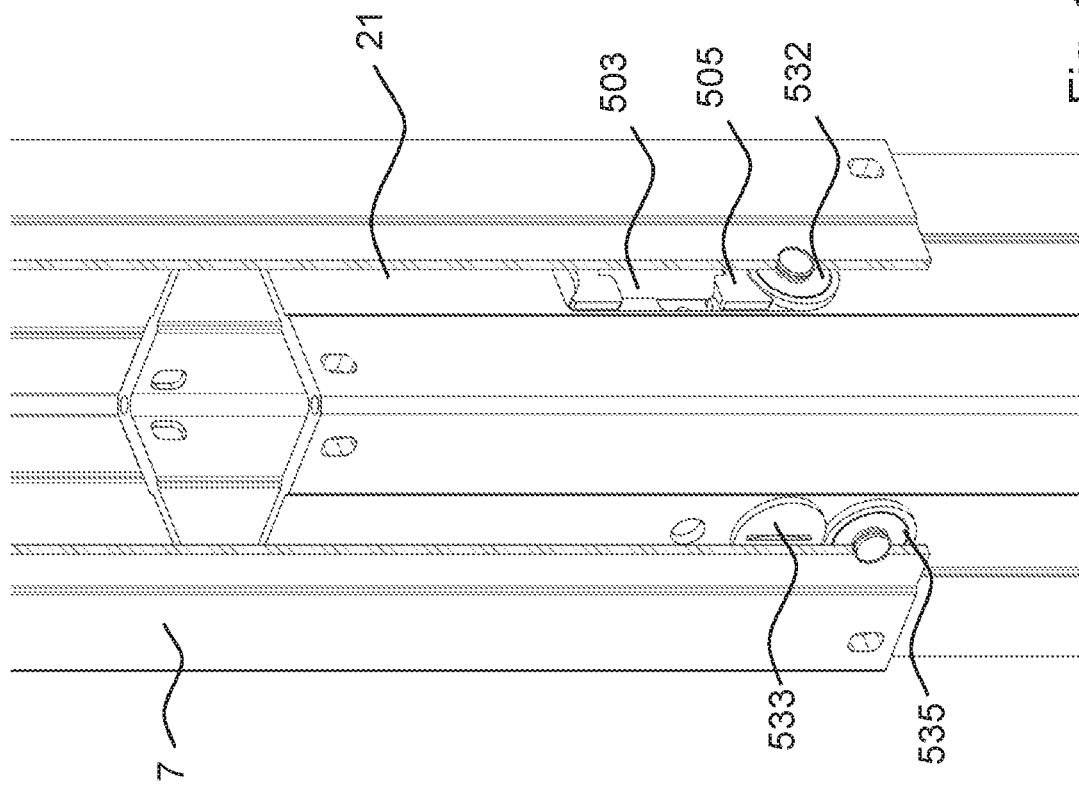
FIGS. 18 and 19 show the shock absorber according to FIG. 13 in the telescopic column.
Figure 18:
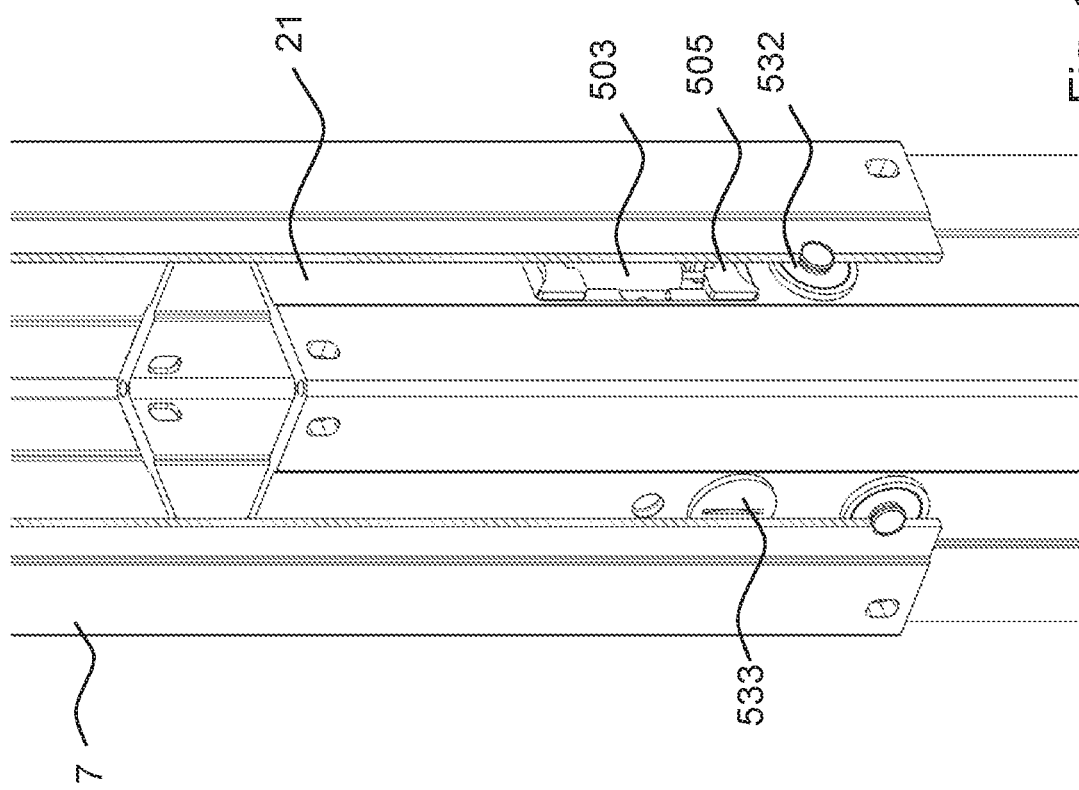

In FIGS. 18 and 19 the mode of operation of the shock absorber 503 in the installed state is illustrated. Two of the column elements 7, 21, 23, 25, and 27 (here 7 and 21) are exemplarily shown. The slot 502 with shock absorber 503 lying therein is disposed in the upper region of the respective inner-lying of the two column elements 21, 23, 25 and 27 (here 21). For this purpose a round stopper 532 is correspondingly attached in the lower region of the respective outer-lying of the column elements 7, 21, 23, and 25 (here 7). The rounding of the stopper 532 is adapted to the round shape 513. With extending of the telescopic column, near the maximum extension length an engaging of the lower receiving element 505 of the shock absorber 503 with the stopper 532 results, so that the plunger 519 is pressed in the cylinder 517. As described above the movement is then damped by the liquid 521, and the column elements are slowly and gently braked and stopped. The end of the movement is depicted in FIG. 19. No hard impacts arise at the end of the movement, whereby the wear is minimized and undesired noises are avoided. For safety a stopper 533 is also attached in column element 7, which stopper 533 comes into engagement with a further stopper 535 in column element 21 if a shock absorber should fail. In addition the shock absorber 503 is relieved in the extended state. In the upper region not depicted here the column element 7 also comprises stoppers that during retracting of the column element 21 come into engagement towards the end of the retracting with the upper receiving element 505 of the shock absorber 503, and brake and stop the movement. Depending on the loads and speeds a plurality of shock absorbers can be used between each two of the column elements; this plurality of shock absorbers can also be used in different side surfaces.

In FIGS. 20 and 21 the monitoring unit 51 is shown in two operating states. It comprises a frame 52 attached inwardly to the column element 7, on which frame 52 a bracket 53 is rotatably secured. End-side a roller 55 is rotatably or fixedly secured to the bracket 53. The cables 35 and 45 are guided downward through the bracket, wherein the cable 45 is in contact with the roller 55, while the cable 35 does not contact the bracket. Between the frame 52 and the bracket 53 a spring 56 is disposed that presses on the bracket with a force below the axis of rotation 57 toward the frame 52. The part of the frame 53 carrying the roller 55 is thereby pulled downward in addition to the weight force of the roller 55, until a state of equilibrium is reached due to the clamping force of the cable 45 against which the roller 55 presses. In the normal state depicted in FIG. 3, i.e., with intact cable 35, the clamping force is generated by the spring 49, via which the cable 45 is connected to the receiving plate 31. Consequently the cable 45 does not then extend vertically downward, but rather is pulled somewhat to the side guided via the roller 55. This normal state is also maintained during extending or retracting of the ceiling stand 1, since the nearly full load hangs on the cable 35. The cable 45 serves primarily as safety- and detector-cable. Should the cable 35 break, the full weight force of the column elements 21, 23, 25, and 27 would be on the receiving plate 31, and the load located thereon would hang on cable 45. Consequently another force would pull on the end of the spring 49, which disrupts the balance. The cable 45 would be more tightly drawn and the bracket 53 impinged with a stronger force, which is thereby deflected upward. The spring 56 is thereby stretched. This state is depicted in FIG. 20, where the cable 45 is stretched nearly vertically downward by the increased downwardly acting force, and the roller 55 is thereby pressed upward.

The monitoring unit 51 is furthermore in the position to detect a break of the cable 45. Also in this case the balance for the spring 49 is disturbed since due to the latter more tension can be transmitted to the cable 45. This state is depicted in FIG. 21. The cable 45 is no longer pulled downward and is therefore correspondingly slack. In comparison to the normal state the force of the spring 56 pulls the bracket 53 downward, whereby the roller 55 is also moved downward.

With respect to their loadability the cables 35 and 45 are designed such that they are each in the position to carry the permitted total load alone. In this respect in the normal state only the cable 35 is loaded, while the cable 45 serves only as a safety cable. However, in the case of the breakage of one of the cables 35 or 45 there is a potential safety risk, with the result that the drive is to be shut off or at least an alarm is to be issued. As already explained, the monitoring unit 51 is also in the position to detect a break of each of the cables 35 and 45 by a change of the position of the bracket.

Figure 22:
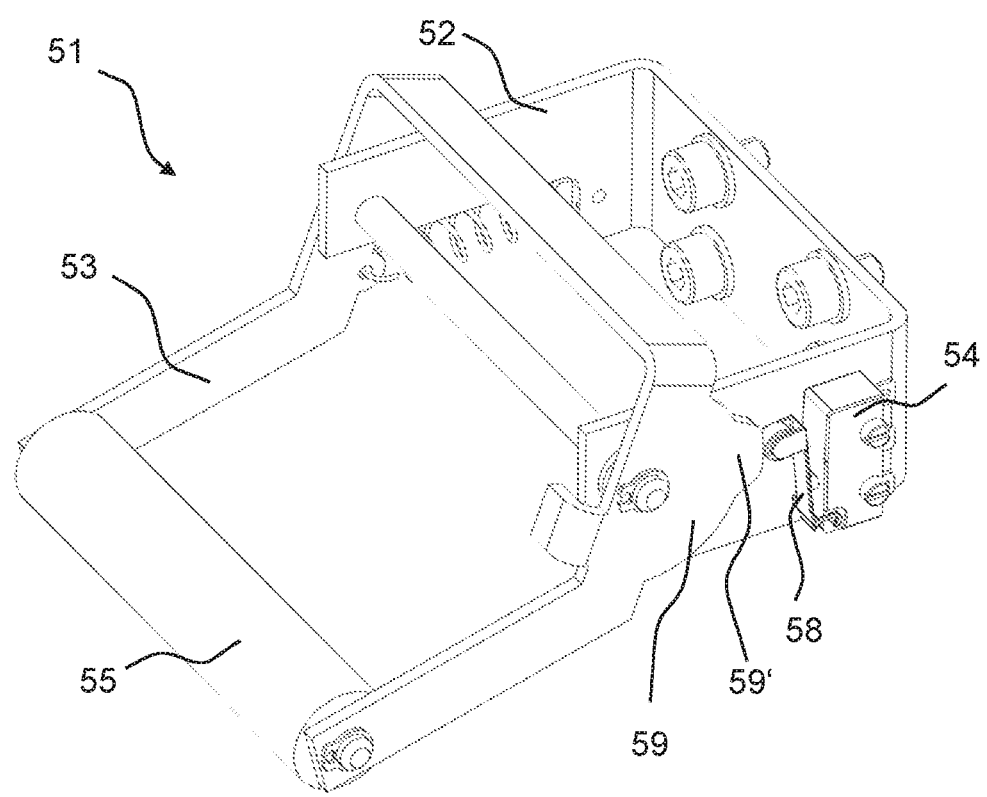
Figure 23:
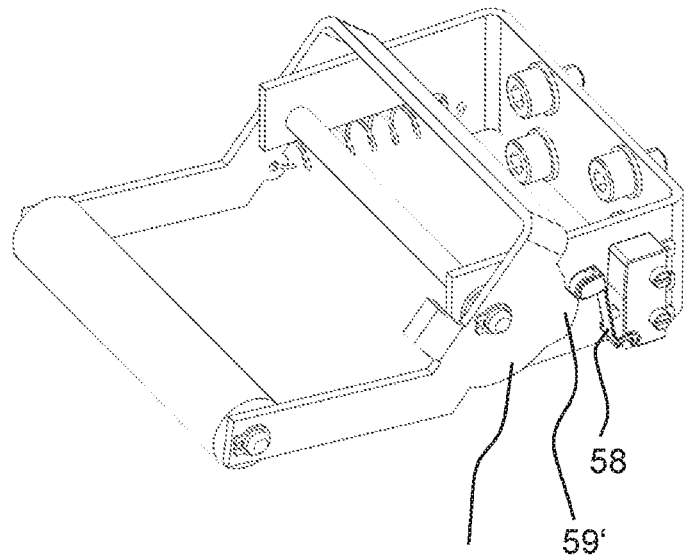
Figure 24:
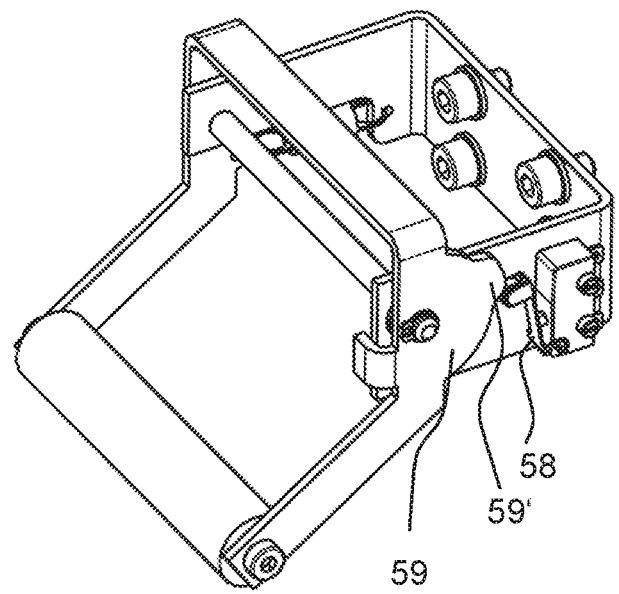

In FIG. 22 the monitoring unit 51 is depicted separately from the other viewing direction. On the frame 52 a switch is mounted that comprises a switch housing 54 and can be switched via a movable arm 58. Here the arm 58 is formed from a curved metal plate that resiliently pushes the arm 58 away from the switch housing 54. The arm 58 is in contact with a semicircular formation 59 formed on the bracket 53, which formation 59 in turn includes a projection 59'. With rotating of the bracket 53 the spacing between the arm 58 and the switch housing 54 is changed. With contact of the arm 58 with the projection 59' the arm 58 is pushed relatively close to the switch housing 54 and thus closes the switch. This position is shown in FIG. 22 and corresponds to the already explained normal state. With rupturing of one of the cables 35 or 45 the bracket 53 is moved upward or downward, whereby the arm 58 comes into contact with the formation 59 above or below the projection 59'. These states are depicted in FIGS. 23 (cable 35 broken) and 24 (cable 45 broken). The arm 58 therefore moves away from the switch housing 54 and the switch thereby opens. If one of the cables 35 or 45 breaks, an alarm can thus be issued via connected electronics on the basis of the state of the switch. Likewise the system can be switched off.

Figure 25:
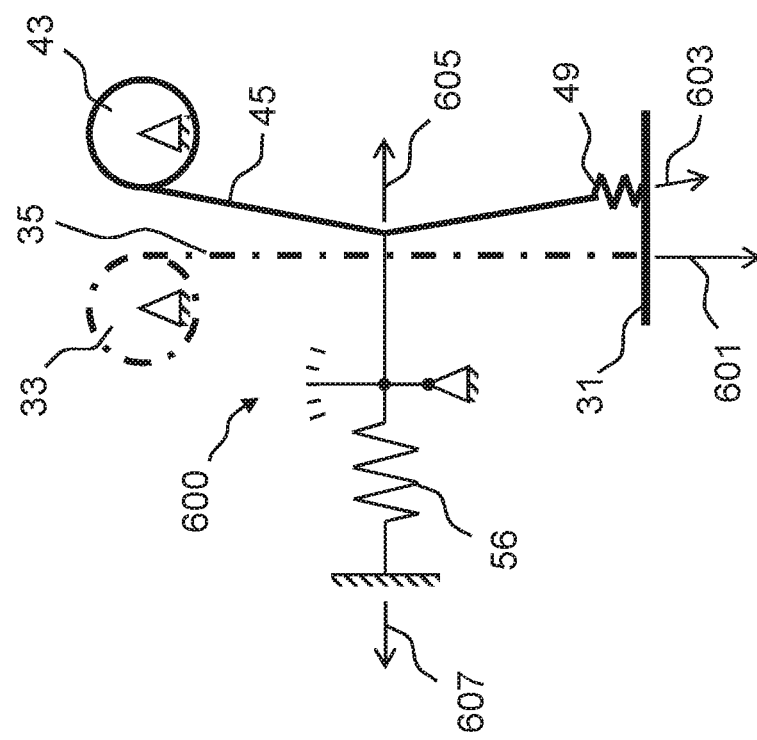

The normal state is schematically depicted in FIG. 25. The receiving plate 31 is connected with both cables 35 and 45, wherein the connection to the cable 45 is effected via the spring 49. The load is distributed on the cables 35 and 45, which is depicted by arrows 601 and 603. The main load acts on the cable 35. The cable 45 is deflected to the left from the vertical position by the spring 56, with the result that a balance to the acting force of the spring 49 arises, which is depicted by arrows 605 and 607. Here the spring 56 is tensioned between a relaxed and a maximally tensed state, which is illustrated by a display 600 only depicted here for illustration.

Figure 26:
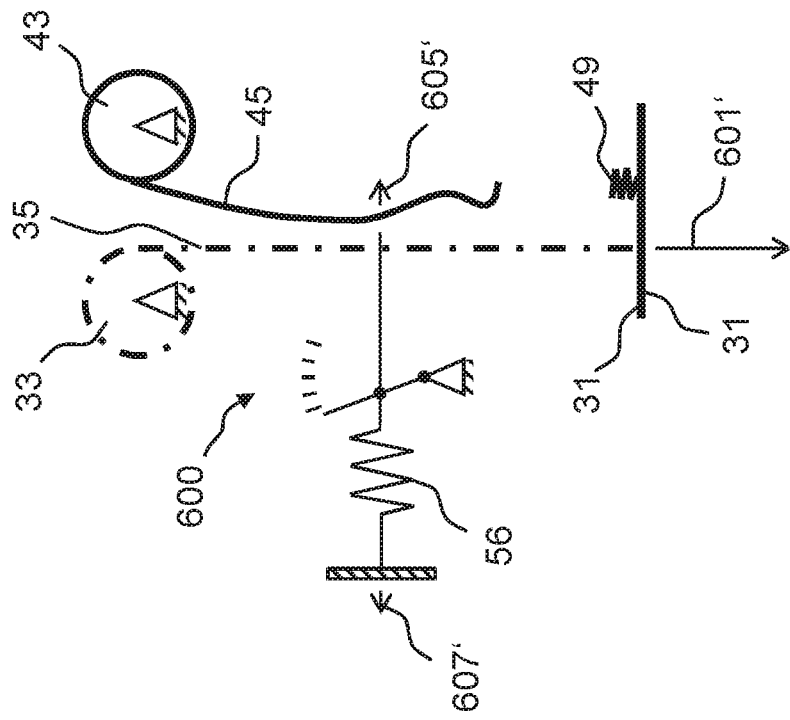

In FIG. 26 the case of a broken cable 45 is depicted. The full load hangs on the cable 35, which is depicted by the long arrow 601'. On the part of the cable 45 a very slight or even no force thereby acts on the spring 65, which is depicted by the shorter arrows 605' and 607'. Thus the spring 56 can relax, which is illustrated by a deflection of the display 600. In this case the switch is opened and an alarm is issued.

In FIG. 27 the case of the broken cable 35 is depicted. The full load thereby hangs on cable 45, which is represented by the longer arrow 603". Accordingly the spring 49 is stretched and the cable 45 tightened. Thus a greater force acts on the spring 56, which is represented by the longer arrows 605" and 607". The spring 56 is thus also stretched, which in turn is illustrated by the deflection of the display 600. Also in this case the switch is opened and an alarm is issued.

However, using the monitoring unit 51 not only the previously described rupturing of the cables 35 or 45 can be detected. Rather, wear of the primarily loaded cable 35 can also be detected. With the use of steel cables, with continuous use fatigue results by breakage or stretching of individual steel fibers. The cable 35 thereby becomes slightly longer. In this respect the balance of the forces on the cable 45 is changed, which is also detectable by use of a force meter. Thus a breakage of a cable is often avoided beforehand by timely exchange.

Using the described safety system, in combination with the drive concept described, an extremely compact and reliable as well as safe telescopic column can be provided that in particular satisfies medical requirements.

Representative, non-limiting examples of the present invention were described above in detail with reference to the attached drawings. This detailed description is merely intended to teach a person of skill in the art further details for practicing preferred aspects of the present teachings and is not intended to limit the scope of the invention. Furthermore, each of the additional features and teachings disclosed above may be utilized separately or in conjunction with other features and teachings to provide improved telescopic column.

Moreover, combinations of features and steps disclosed in the above detailed description may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

REFERENCE NUMBER LIST

1 Ceiling stand
3, 31 Receiving plate

5 Screw hole
7, 21, 23, 25, 27 Column element
9 Housing
11 Motor
17 Drive shaft
33, 43 Cable drum
35, 45 Cable
37, 47 Attachment unit
49, 56 Spring
51 Monitoring unit
52 Frame
53 Bracket
54 Switch housing
55 Roller
57 Axis of rotation
58 Arm
59 Formation
59' Projection
61 Main drive unit
63, 83 Shaft
65, 85 Bearing point
67, 87 Worm gear
69, 89 Coupling unit
81 Safety unit
91, 93 Clutch element
92 Screw
94 Coil spring
101 Base element
102 Screw hole
103a, 103b, 103c, 107a, 107b, 107c Coupling element
105 Shaft seat
106 Groove
109, 109' End
111 Projection
113 Brake housing
500 Side surface
501 Recess
502 Slot
503 Shock absorber
505 Receiving element
507 Center part
509 Guide part
511 Groove
513 Round shape
515 Damping element
517 Cylinder
519 Plunger
521 Liquid
523 Spring
525 Piston
527, 529 Channel
531 Valve
532, 533, 535 Stopper
600 Display
601, 601', 603, 603" Arrow
605, 605', 605" Arrow
607, 607', 607" Arrow

What is claimed is:

1. A telescopic column, comprising:
   at least two telescopic elements linearly movable with respect to one another, and
   a drive system, containing:
      a drive unit including a first clutch element,
      an output unit including a shaft, a windable connecting element and a second clutch element connected to the shaft such that the second clutch element and the shaft rotate together, wherein the connecting element is connected to the shaft and at least one of the movable telescopic elements,
      a brake unit configured to transmit a sufficiently strong retaining force onto the second clutch element that the telescopic elements are held in their relative position with respect to each other,
      the brake unit is further configured such that applying a drive moment to the first clutch element reduces the retaining force such that the telescopic elements are movable relative to each other, and
      the brake unit is further configured such that with applying an output-side torque to the second clutch element increases the retaining force acting on the second clutch element.

2. The telescopic column according to claim 1, wherein the connecting element is a cable, a belt, or a chain.

3. The telescopic column according to claim 1, wherein the brake unit includes a spring element and a brake surface, wherein the spring element is preloaded into frictional contact with the brake surface for generating the retaining force, and wherein bringing brining the spring element into operative contact with the clutch elements changes a spring tension of the spring element.

4. The telescopic column according to claim 3, wherein the operative contact between the clutch elements and the spring element is generatable by at least one coupling element formed on each of the clutch elements and at least one further coupling element, corresponding thereto, of the spring element.

5. The telescopic column according to claim 3, wherein each of the clutch elements includes at least two coupling elements, and the spring element includes two coupling elements, each corresponding to one of the coupling elements of the clutch elements, wherein rotating the first clutch element in a first direction brings a first one of the coupling elements of the first clutch element into operative contact with the first coupling element of the spring element, and rotating the clutch element in a second direction brings the second coupling element of the first clutch element enters into operative contact with the second coupling element of the spring element, so that independent of the respective direction of rotation of the respective coupling element an operative contact changing the spring tension identically is generatable.

6. The telescopic column according to claim 5, wherein each of the clutch elements includes at least one third coupling element, wherein the coupling elements of the clutch elements are configured such that each one of the coupling elements of both clutch elements is bringable into operative contact as soon as one of the first or second coupling elements of the clutch elements is in operative contact with one of the coupling elements of the spring element.

7. The telescopic column according to claim 1, wherein the clutch elements and the brake unit form a coil-spring coupling unit.

8. The telescopic column according to claim 1, wherein the connecting element is connected to the shaft such that rotating the shaft rotates the connecting element.

9. The telescopic column according to claim 1, further comprising a further drive system that is constructed analogously to the drive system and functions as a redundant drive system.

10. A ceiling-hanging telescopic system including the telescopic column according to claim 1.

11. A telescopic column, comprising:
- a first telescopic element telescopically mounted in a second telescopic element, the first telescopic element and the second telescopic element being movable with respect to one another in a direction of a gravitational force and in a direction opposite the direction of the gravitational force;
- a motor;
- a spool on a shaft;
- a cable connected from the spool to the first telescopic element such that rotating the spool in a first direction winds the cable around the shaft and moves the first telescopic element in the direction opposite the direction of gravitational force, and
- a clutch and brake system for allowing the motor to rotate the spool in the first direction and for selectively and passively preventing the spool from rotating in the second direction.

12. The telescopic column according to claim 11, wherein the clutch and brake system comprises a cylindrical housing surrounding a portion of the shaft and a coil spring wrapped around the shaft inside the housing.

13. A telescopic column, comprising:
- a first telescopic element telescopically mounted in a second telescopic element, the first telescopic element and the second telescopic element being movable with respect to one another in a direction of a gravitational force and in a direction opposite the direction of the gravitational force;
- a motor;
- a spool on a shaft;
- a cable connected from the spool to the first telescopic element such that rotating the spool in a first direction winds the cable around the shaft and moves the first telescopic element in the direction opposite the direction of gravitational force and such that rotating the spool in a second direction opposite the first direction allows the first telescopic column to move in the direction of the gravitational force, and
- a first clutch element fixedly mounted on the shaft for rotation with the shaft,
- a housing surrounding a portion of the shaft,
- a coil spring mounted around the portion of the shaft inside the housing, and
- a second clutch element operatively connected to the motor and in contact with the coil spring, wherein the first clutch element, second clutch element and coil spring are configured such that rotating the shaft and first clutch element in the second direction enlarges a diameter of the coil spring and presses the coil spring against an inside of the housing to prevent further rotation of the shaft and such that rotating the second clutch element in the first direction reduces the diameter of the coil spring and moves the coil spring away from the inside of the housing and winds the spool in the first direction.

* * * * *